US010683252B2

(12) United States Patent
Hosoi et al.

(10) Patent No.: US 10,683,252 B2
(45) Date of Patent: Jun. 16, 2020

(54) PRODUCTION METHOD FOR 1,2,2,2-TETRAFLUOROETHYL DIFLUOROMETHYL ETHER (DESFLURANE)

(71) Applicant: Central Glass Company, Limited, Ube-shi, Yamaguchi (JP)

(72) Inventors: Kenji Hosoi, Kawagoe (JP); Mineo Watanabe, Kawagoe (JP); Hideaki Imura, Fujimino (JP); Kensuke Hirotaki, Kawagoe (JP); Naoya Ueshima, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 16/474,136

(22) PCT Filed: Dec. 15, 2017

(86) PCT No.: PCT/JP2017/045083
§ 371 (c)(1),
(2) Date: Jun. 27, 2019

(87) PCT Pub. No.: WO2018/123649
PCT Pub. Date: Jul. 5, 2018

(65) Prior Publication Data
US 2019/0345086 A1 Nov. 14, 2019

(30) Foreign Application Priority Data

| Dec. 29, 2016 | (JP) | 2016-257221 |
| Dec. 29, 2016 | (JP) | 2016-257222 |
| Dec. 29, 2016 | (JP) | 2016-257223 |
| Jan. 13, 2017 | (JP) | 2017-004071 |
| Dec. 7, 2017 | (JP) | 2017-234919 |

(51) Int. Cl.
C07C 41/22 (2006.01)
C07C 41/01 (2006.01)
C07C 45/63 (2006.01)

(52) U.S. Cl.
CPC .............. *C07C 41/22* (2013.01); *C07C 41/01* (2013.01); *C07C 45/63* (2013.01)

(58) Field of Classification Search
CPC .......... C07C 41/22; C07C 41/01; C07C 45/63
See application file for complete search history.

(56) References Cited

U.S. PATENT DOCUMENTS

| 3,017,436 A * | 1/1962 | Hamilton ............... C07C 45/63 568/466 |
| 3,897,502 A | 7/1975 | Russell et al. |
| 3,981,927 A | 9/1976 | Siegemund et al. |
| 4,579,976 A * | 4/1986 | Cheminal ............... C07C 45/63 568/458 |
| 4,762,856 A | 8/1988 | Terrell |
| 4,874,901 A | 10/1989 | Halpern et al. |
| 4,972,040 A | 11/1990 | Robin et al. |
| 5,015,781 A | 5/1991 | Robin et al. |
| 5,026,924 A | 6/1991 | Cicco |
| 5,185,474 A | 2/1993 | O'Neill |
| 5,196,600 A | 3/1993 | O'Neill |
| 5,205,914 A | 4/1993 | Rozov et al. |
| 5,278,342 A | 1/1994 | O'Neill et al. |
| 5,446,211 A | 8/1995 | O'Neill et al. |
| 5,504,263 A | 4/1996 | Burgess et al. |
| 5,543,055 A | 8/1996 | O'Neill et al. |
| 5,696,308 A | 12/1997 | Burgess et al. |
| 5,750,807 A | 5/1998 | Burgess et al. |
| 6,054,626 A | 4/2000 | Chambers et al. |
| 6,225,511 B1 | 5/2001 | Chambers et al. |
| 6,800,786 B1 | 10/2004 | Rozov et al. |
| 2003/0209685 A1 | 11/2003 | Robin et al. |
| 2008/0125589 A1 | 5/2008 | Ishii et al. |
| 2008/0132731 A1 | 6/2008 | Swinson et al. |
| 2010/0185020 A1 | 7/2010 | Hariharan et al. |
| 2010/0249302 A1 | 9/2010 | Sugiura et al. |
| 2011/0082313 A1 | 4/2011 | Ishii et al. |

FOREIGN PATENT DOCUMENTS

| DE | 23 61 058 A1 | 6/1975 |
| DE | 26 56 545 A1 | 6/1978 |
| JP | 50-076007 A | 6/1975 |
| JP | 2-104545 A | 4/1990 |
| JP | 2-279646 A | 11/1990 |

(Continued)

OTHER PUBLICATIONS

International Search Report (PCT/ISA/210) issued in PCT Application No. PCT/JP2017/045082 dated Jan. 16, 2018 with English translation (four (4) pages).
Japanese-language Written Opinion (PCT/ISA/237) issued in PCT Application No. PCT/JP2017/045082 dated Jan. 16, 2018 (three (3) pages).
Ishii et al., "Trifluoroacetaldehyde", Journal of Synthetic Organic Chemistry, 1999, pp. 102-103, vol. 57, No. 10, with English abstract (four (4) pages).
Bagnall et al., "New Inhalation Anesthetics: III Fluorinated Aliphatic Ethers", Journal of Fluorine Chemistry, 1979, pp. 123-140, vol. 13, (18 pages).
International Search Report (PCT/ISA/210) issued in PCT Application No. PCT/JP2017/045083 dated Jan. 23, 2018 with English translation (four (4) pages).

(Continued)

*Primary Examiner* — Rosalynd A Keys
(74) *Attorney, Agent, or Firm* — Crowell & Moring LLP

(57) ABSTRACT

Fluoral is obtained by gas-phase fluorination of chloral in the presence of a catalyst and then reacted with trimethyl orthoformate, thereby readily forming 1,2,2,2-tetrafluoroethyl methyl ether as an intermediate for production of desflurane. 1,2,2,2-Tetrafluoroethyl difluoromethyl ether (desflurane) is produced with high yield from the thus-formed 1,2,2,2-tetrafluoroethyl methyl ether by chlorination and fluorination. This method enables efficient industrial-scale production of desflurane useful as an inhalation anesthetic.

22 Claims, No Drawings

(56) References Cited

FOREIGN PATENT DOCUMENTS

| | | |
|---|---|---|
| JP | 4-273839 A | 9/1992 |
| JP | 6-87777 A | 3/1994 |
| JP | 6-192154 A | 7/1994 |
| JP | 6-298693 A | 10/1994 |
| JP | 7-502037 A | 3/1995 |
| JP | 7-291881 A | 11/1995 |
| JP | 11-506742 A | 6/1999 |
| JP | 2006-290870 A | 10/2006 |
| JP | 2008-150385 A | 7/2008 |
| JP | 2009-286731 A | 12/2009 |
| JP | 2010-533211 A | 10/2010 |
| JP | 2010-254678 A | 11/2010 |
| WO | WO 2006/076324 A2 | 7/2006 |

OTHER PUBLICATIONS

Japanese-language Written Opinion (PCT/ISA/237) issued in PCT Application No. PCT/JP2017/045083 dated Jan. 23, 2018 (three (3) pages).

Fenneteau et al., "Liebeskind-Srogl Cross-Coupling on γ-carbozyl-γ-butyrolactone Derivatives: Application to the Side Chain of Amphidinolides C and F", Tetrahedron Letters, 2015, pp. 3758-3761, vol. 56, (four (4) pages).

Siegemund, "Darstellung von Trifluoracetaldehyd-alkylhalbacetalen und deren Umwandlung in (2,2,2,-Trifluor-1-halogenaethyl)alkylaether", Chem. Ber., 1973, pp. 2960-2968, (nine (9) pages).

\* cited by examiner

PRODUCTION METHOD FOR 1,2,2,2-TETRAFLUOROETHYL DIFLUOROMETHYL ETHER (DESFLURANE)

FIELD OF THE INVENTION

The present invention relates to a method for producing 1,2,2,2-tetrafluoroethyl difluoromethyl ether (desflurane).

BACKGROUND ART

It is known that 1,2,2,2-tetrafluoroethyl difluoromethyl ether, also called desflurane, is an important inhalation anesthetic. This inhalation anesthetic compound is very low in in-vivo metabolism and thus is widely used as a biologically friendly and highly safe drug. One known production method of desflurane is to fluorinate its precursor compound such as 1-chloro-2,2,2-trifluoroethyl difluoromethyl ether ($CF_3CHClOCHF_2$; also called isoflurane), 2,2,2-trifluoroethyl difluoromethyl ether ($CF_3CH_2OCHF_2$) or 1,2,2,2-tetrafluoroethyl dichloromethyl ether ($CF_3CHFOCHCl_2$). There is known a method of halogen-exchange fluorination of isoflurane with the use of an alkali metal fluoride (see Patent Document 1), with the use of bromine trifluoride (see Patent Documents 2 and 3) or with the use of hydrogen fluoride (see Patent Documents 3, 4, 5 and 6). There is known a method of direct fluorination of 2,2,2-trifluoroethyl difluoromethyl ether with the use of fluorine gas (see Patent Document 8) or with the use of a high-order metal fluoride compound (see Patent Documents 9 and 10). There is known a method of fluorination of 1,2,2,2-tetrafluoroethyl dichloromethyl ether with the use of hydrogen fluoride (see Patent Document 11).

PRIOR ART DOCUMENTS

Patent Documents

Patent Document 1: U.S. Pat. No. 4,874,901
Patent Document 2: U.S. Pat. No. 4,762,856
Patent Document 3: U.S. Pat. No. 5,015,781
Patent Document 4: Japanese Laid-Open Patent Publication No. H2-279646
Patent Document 5: U.S. Pat. No. 6,800,786
Patent Document 6: International Publication No. 2006-076324
Patent Document 7: Japanese Translation of International Application Publication No. 2010-533211
Patent Document 8: U.S. Pat. No. 3,897,502
Patent Document 9: Japanese Laid-Open Patent Publication No. H4-273839
Patent Document 10: Japanese Laid-Open Patent Publication No. H6-192154
Patent Document 11: German Patent No. 2361058

SUMMARY OF THE INVENTION

Problems to be Solved by the Invention

Because of the properties of the ether (—O—) moiety-containing compound, the production of the desflurane presents the problem of generation of a by-product by cleavage of an ether moiety of the desflurane during the fluorination under severe conditions. In the conventional production methods, the rate of conversion from the starting raw material to the target desflurane is low considering that the starting raw material is expensive. The conventional production methods are thus not be efficient methods.

The method disclosed in Patent Document 1 is difficult to industrially implement due to its high-temperature and high-pressure fluorination conditions. Further, the method disclosed in Patent Document 1 is low in yield. The method disclosed in Patent Document 2 or 3 uses a highly toxic and corrosive reagent which is difficult to handle. The method disclosed in Patent Document 4 or 5 enables middle-yield production of the target desflurane by liquid-phase fluorination of isoflurane with hydrogen fluoride in the presence of antimony pentachloride as a catalyst at around room temperature. In the method disclosed in Patent Document 4 or 5, however, there is generated a large amount of impurities as by-products by cleavage of an ether moiety of the isoflurane as the raw material or the desflurane as the target product due to the reasons that: the hydrogen fluoride itself is an oxidizing substance; and the antimony pentachloride is generally high in reactivity. The method disclosed in Patent Document 6 involves gas-phase fluorination in the presence of a chromia catalyst, but merely shows a middle conversion rate and does not provide a satisfactory result. The method disclosed in Patent Document 7 involves gas-phase fluorination in the presence of an antimony-supported activated carbon catalyst, but does not always show a high conversion rate.

On the other hand, the method disclosed in Patent Document 8 has a risk of explosion and a problem of handling inconvenience. Furthermore, the method disclosed in Patent Document 8 shows a low conversion rate (30%) and a low target product yield and thus is difficult to implement as an industrial production method of inhalation anesthetic. The method disclosed in Patent Document 9 or 10 is economically unfavorable due to the reason that the high-order metal fluoride compound needs to be used in a large excess amount in order for the reaction to proceed smoothly. The method disclosed in Patent Document 11 shows a low to middle conversion rate and thus is difficult to implement as a production method of inhalation anesthetic. As mentioned above, the problems remain unresolved in these disclosed methods. Even though Patent Document 11 specifically discloses a reaction example in which 1,2,2,2-tetrafluoroethyl dichloromethyl ether was fluorinated with hydrogen fluoride in a liquid phase in the presence of an antimony pentachloride catalyst at around room temperature, the yield of the target desflurane was low (21%) in the disclosed reaction example.

Under the above circumstances, there has been a strong demand to develop a method for efficiently producing desflurane from a readily available starting raw material with the use of a safe-to-handle fluorination agent.

Means for Solving the Problems

The present inventors have made extensive researches in view of the above problems. As a result of the researches, the present inventors have newly found that desflurane of the formula [5] is efficiently produced through the steps of: forming 2,2,2-trifluoroacetaldehyde (also called fluoral; hereinafter sometimes simply referred to as "fluoral" in the present specification) by continuous fluorination of 2,2,2-trichloroacetaldehyde of the formula [1] (also called chloral; hereinafter sometimes simply referred to as "chloral" in the present specification) with hydrogen fluoride; selectively forming 1,2,2,2-tetrafluoroethyl methyl ether by reaction of the 2,2,2-trifluoroacetaldehyde with hydrogen fluoride and trimethyl orthoformate; forming 1,2,2,2-tetrafluoroethyl dichloromethyl ether of the formula [4] as a desflurane precursor by chlorination of the 1,2,2,2-tetrafluoroethyl methyl ether in the presence of a radical initiator or under light irradiation; and then reacting the 1,2,2,2-tetrafluoroethyl dichloromethyl ether with hydrogen fluoride. The present invention is based on this finding.

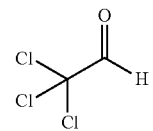

[1]

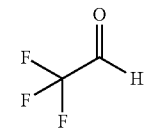

[2]

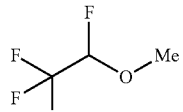

[3]

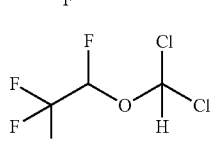

[4]

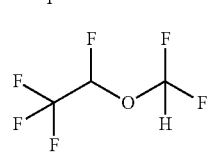

[5]

The fluorination step of the 1,2,2,2-tetrafluoroethyl dichloromethyl ether corresponds to the reaction example of Patent Document 11. However, the production method according to the present invention enables much more advantageous production of the target desflurane than the conventional method by using chloral, which is industrially available at very low cost, as the starting raw material and adopting four steps as mentioned above, with almost no generation of difficult-to-separate impurities in each step. It can thus be said that the production method according to the present invention is particularly preferable for industrial production of desflurane.

There has not been known a production method of desflurane which uses 2,2,2-trichloroacetaldehyde as a starting raw material and goes through the steps of fluorinating the 2,2,2-trichloroacetaldehyde in a gas phase to form 2,2,2-trifluoroacetaldehyde, efficiently converting the 2,2,2-trifluoroacetaldehyde to 1,2,2,2-tetrafluoroethyl methyl ether, chlorinating the 1,2,2,2-tetrafluoroethyl methyl ether and then fluorinating the chlorination product as disclosed in the present invention.

Namely, the present invention provides a production method of 1,2,2,2-tetrafloroethyl difluoromethyl ether (desflurane) as set forth in the following inventive aspects 1 to 22.

Inventive Aspect 1

A production method of 1,2,2,2-tetrafloroethyl difluoromethyl ether (desflurane) of the formula [5], comprising the following four steps:

a first step of reacting 2,2,2-trichloroacetaldehyde of the formula [1] with hydrogen fluoride in a gas phase in the presence of a catalyst, thereby obtaining 2,2,2-trifluoroacetaldehyde of the formula [2];
a second step of reacting the 2,2,2-trifluoroacetaldehyde obtained in the first step with hydrogen fluoride and trimethyl orthoformate, thereby obtaining 1,2,2,2-tetrafluoroethyl methyl ether of the formula [3];
a third step of reacting the 1,2,2,2-tetrafluoroethyl methyl ether obtained in the second step with chlorine ($Cl_2$) in the presence of a radical initiator or under light irradiation, thereby obtaining 1,2,2,2-tetrafluoroethyl dichloromethyl ether of the formula [4]; and a fourth step of reacting the 1,2,2,2-tetrafluoroethyl dichloromethyl ether obtained in the third step with hydrogen fluoride, thereby obtaining 1,2,2,2-tetrafloroethyl difluoromethyl ether (desflurane) of the formula [5].

Inventive Aspect 2

The production method according to Inventive Aspect 1, wherein the catalyst used in the first step is a metal compound-supported catalyst having, supported on a metal oxide or activated carbon, a metal compound containing at least one metal selected from the group consisting of chromium, titanium, manganese, iron, nickel, cobalt, magnesium, zirconium and antimony.

Inventive Aspect 3

The production method according to Inventive Aspect 2, wherein the metal compound is at least one kind of metal halide or metal oxyhalide selected from the group consisting of a fluoride, a chloride, a fluorochloride, an oxyfluoride, an oxychloride and an oxyfluorochloride of the at least one metal.

Inventive Aspect 4

The production method according to Inventive Aspect 2 or 3, wherein the metal oxide is at least one kind selected from the group consisting of alumina, zirconia, titania, chromia and magnesia.

Inventive Aspect 5

The production method according to any one of Inventive Aspects 1 to 4, wherein the 2,2,2-trifluoroacetaldehyde obtained in the first step is used as it is, without purification operation, as a raw material in the second step.

Inventive Aspect 6

The production method according to any one of Inventive Aspects 1 to 5, wherein, in the second step, the reaction is conducted without the use of an organic solvent.

Inventive Aspect 7

The production method according to any one of Inventive Aspects 1 to 6, wherein the radical initiator used in the third step is at least one kind selected from the group consisting of an organic peroxide and an azo-based radical initiator.

Inventive Aspect 8

The production method according to any one of Inventive Aspects 1 to 6, wherein the light irradiation used in the third step is at least one kind selected from the group consisting of those from a mercury lamp, an ultraviolet LED, an organic EL, an inorganic EL, an ultraviolet laser and a halogen lamp.

Inventive Aspect 9

The production method according to any one of Inventive Aspects 1 to 8, wherein, in the third step, the reaction is conducted in the presence of a fluoride ion scavenger.

Inventive Aspect 10

The production method according to Inventive Aspect 9, wherein fluoride ion scavenger is at least one kind selected from the group consisting of a halide of an alkali metal, a sulfate of an alkali metal, a hydroxide of an alkaline-earth metal, a halide of an alkaline-earth metal, a sulfate of an alkaline-earth metal, a hydroxide of a Group 13 metal of the periodic table, a halide of a Group 13 metal of the periodic table and a sulfate of a Group 13 metal of the periodic table.

Inventive Aspect 11

The production method according to any one of Inventive Aspects 1 to 10, wherein, in the third step, the reaction is conducted with the use of a reaction solvent.

Inventive Aspect 12

The production method according to any one of Inventive Aspects 1 to 11, wherein, in the third step, the 1,2,2,2-tetrafluoroethyl dichloromethyl ether of the formula [4] is obtained as a mixture thereof with a 1,2,2,2-tetrafluoroethyl chloromethyl ether of the formula [7]

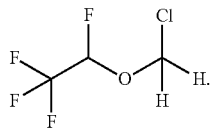

[7]

Inventive Aspect 13

The production method according to Inventive Aspect 12, further comprising performing distillation purification on the mixture to separate and remove the 1,2,2,2-tetrafluoroethyl chloromethyl ether of the formula [7] from the mixture.

Inventive Aspect 14

The production method according to Inventive Aspect 13, wherein the 1,2,2,2-tetrafluoroethyl chloromethyl ether of the formula [7] separated and removed by the distillation purification is recovered and used as a raw material in the third step.

Inventive Aspect 15

The production method according to any one of Inventive Aspects 1 to 14, wherein, in the fourth step, the reaction is conducted in a gas phase.

Inventive Aspect 16

The production method according to any one of Inventive Aspects 1 to 15, wherein, in the fourth step, the reaction is conducted in the presence of a catalyst.

Inventive Aspect 17

The production method according to Inventive Aspect 16, wherein the catalyst used in the fourth step is at least one kind selected from the group consisting of tin tetrachloride, tin dichloride, tin tetrafluoride, tin difluoride, titanium tetrachloride, antimony dichloride, antimony pentachloride and antimony pentafluoride.

Inventive Aspect 18

The production method according to any one of Inventive Aspects 1 to 15, wherein, in the fourth step, the reaction is conducted without the presence of a catalyst.

Inventive Aspect 19

The production method according to any one of Inventive Aspects 1 to 14, wherein, in the fourth step, the reaction is conducted in a liquid phase.

Inventive Aspect 20

The production method according to Inventive Aspect 19, wherein, in the fourth step, the reaction is conducted in the liquid phase in a temperature range of −10° C. to +150° C. and a pressure range of 0.1 MPa to 2.0 MPa (on the basis of absolute pressure; the same applies to the following).

Inventive Aspect 21

The production method according to any one of Inventive Aspects 1 to 14, wherein, in the fourth step, the reaction is conducted by reacting the 1,2,2,2-tetrafluoroethyl dichloromethyl ether with a "salt or complex of an organic base and the hydrogen fluoride" in the liquid phase.

Inventive Aspect 22

The production method according to Inventive Aspect 21, wherein the organic base in the "salt or complex of the organic base and the hydrogen fluoride" is at least one kind selected from the group consisting of triethylamine, diisopropylethylamine, tri-n-butylamine, pyridine, 2,6-lutidine and 1,8-diazabicyclo[5.4.0]undec-7-ene.

The present invention achieves the effects of efficiently producing 1,2,2,2-tetrafluoroethyl difluoromethyl ether (desflurane) by using readily available chloral as the starting raw material and going through the above-mentioned steps with various safe-to-handle reagents.

DETAILED DESCRIPTION OF THE EMBODIMENTS

Hereinafter, the present invention will be described in detail below. It should be understood that the present invention is not limited to the following embodiments and can be embodied as appropriate, based on the common knowledge of those skilled in the art, within the range that does not impair the effects of the present invention.

The production method according to the present invention includes the above-mentioned four steps. The scheme of the respective steps is shown below.

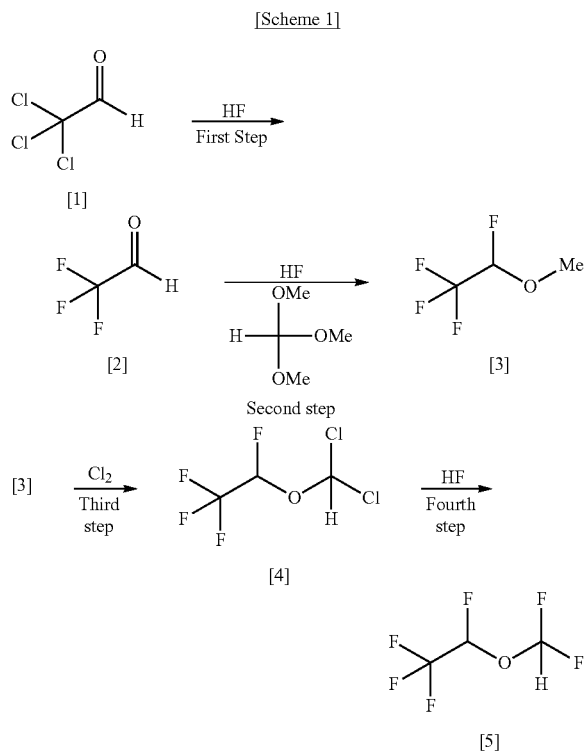

[First Step]

First, the first step will be explained below. In the first step, 2,2,2-trifluoroacetaldehyde of the formula [2] is formed by reaction of 2,2,2-trichloroacetaldehyde of the formula [1] with hydrogen fluoride in a gas phase in the presence of a catalyst.

The 2,2,2-trichloroacetaldehyde of the formula [1] used as the starting raw material in the first step can be a commercially available product (such as a product of Tokyo Chemical Industry Co., Ltd.) or can be prepared by a method disclosed in any technical literature (such as Tetrahedron Letters, 56 (24), 3758-3761, 2015).

The first step is performed by using a reactor made of a material substantially inert to hydrogen fluoride and, under a controlled temperature, introducing the chloral into a reaction zone of the reactor filled with the catalyst. The reactor used in the first step is generally tubular in shape. Examples of the reactor are those made of metal materials such as stainless steel, Hastelloy™, platinum and the like and those formed with internal linings of tetrafluoroethylene resin, chlorotrifluoroethylene resin, vinylidene fluoride resin, PFA resin and the like. The reactor is preferably of the type in which the reaction can be sufficiently carried out under atmospheric pressure or pressurized condition.

The catalyst used in the first step is preferably a metal compound-supported catalyst having, supported on a metal oxide or activated carbon, a metal compound containing at least one metal selected from the group consisting of chromium, titanium, manganese, iron, nickel, cobalt, magnesium, zirconium and antimony. The metal compound is preferably at least one kind of metal halide or metal oxyhalide selected from the group consisting of a fluoride, a chloride, a fluorochloride, an oxyfluoride, an oxychloride and an oxyfluorochloride. The metal oxide used as the support material is preferably at least one kind selected from the group consisting of alumina, zirconia, titania, chromia and magnesia. The support material may be fluorinated. (For example, fluorinated alumina etc. can be used as the support material.) Among others, preferred is the catalyst in which the chromium compound is supported on the metal oxide or activated carbon.

In the case of using the catalyst in which the metal compound is supported on the support material, the amount of the metal compound supported is preferably 0.1 to 100 mass parts, more preferably 1 to 50 mass parts, per 100 mass parts of the support material. As will be explained in the after-mentioned Preparation Example 1, alumina used as the metal oxide support material is generally of the kind obtained by forming a precipitate from an aqueous aluminum salt solution with the addition of ammonia etc. and subjecting the precipitate to molding and dewatering. In ordinary cases, □-alumina commercially available as a catalyst support or a drying agent is preferably used There is no particular limitation on the method for preparation of the catalyst (metal compound-supported catalyst). The catalyst can be prepared by e.g. impregnating or spraying an aluminum oxide such as □-alumina with a solution of a soluble compound of at least one kind of metal selected from the group consisting of chromium, manganese, nickel, cobalt and iron, drying the resulting metal compound-supported aluminum oxide, and then, converting the aluminum oxide support material to fluorinated alumina through partial or complete fluorination with a fluorinating agent such as hydrogen fluoride. It is preferable to, in the final stage of preparation of the catalyst, feed hydrogen fluoride at a temperature higher than or equal to the temperature of the fluorination reaction. This treatment is generally preferably performed at a temperature of 200 to 500° C., more preferably 300 to 400° C.

There is no particular limitation on the kind of the soluble compound as long as the soluble compound is an oxide or salt of the above-mentioned meta which is soluble in a solvent such as water, ethanol or acetone. The soluble metal compound can be a nitrate, a chloride, a sulfate, a carbonate, an acetate or the like. Preferred examples of the soluble metal compound are chromium nitrate, chromium trichloride, chromium trioxide, potassium dichromate, manganese nitrate, manganese chloride, manganese dioxide, nickel nitrate, nickel chloride, cobalt nitrate, cobalt chloride, iron nitrate, iron chloride and the like. These compounds may be in hydrate form. The metal valence of the soluble metal compound is arbitrary. Regardless of how the catalyst is prepared, it is effective to prevent a change in the composition of the catalyst during the reaction by treating the catalyst with a fluorination agent such as hydrogen fluoride at a temperature higher than or equal to the predetermined reaction temperature before the use of the catalyst.

Examples of the activated carbon used as the support material are: plant-based activated carbons produced using wood, wood charcoal, coconut shell charcoal, palm shell charcoal, raw ash etc. as raw materials; coal-based activated carbons produced using peat coal, lignite, brown coal, bituminous coal, anthracite coal etc. as raw materials; petroleum-based activated carbons produced using petroleum pitch, oil carbon etc. as raw materials; and synthetic resin-based activated carbons such as carbonized polyvinylidene chloride. These activated carbons are commercially available and can be selected for use. For example, there can be used bituminous coal activated carbon (available as granular activated carbon BPL from Calgon Mitsubishi Chemical Corporation) or coconut shell activated carbon (available as G2c, G2x, GS3c, GS3x, C2c, C2x, X2M from Japan EnviroChemicals Ltd. or as PCB from Calgon Mitsubishi Chemical Corporation). The activated carbon is however not limited to these kinds. In general, the activated carbon is used in granular form. The granular shape and size of the activated carbon is not particularly limited and can be selected as appropriate within the range of common knowledge as long as the activated carbon is adaptable to the reactor. The activated carbon can be in various shapes such as spherical shape, fibrous shape, powder shape and honeycomb shape. In the present invention, it is preferable that the activated carbon used is large in specific area. The specific surface and pore volume of the activated carbon can be within the specifications of commercially available activated carbons. The activated carbon preferably has a specific surface of larger than 400 $m^2/g$ and a pore volume of larger than 0.1 $cm^3/g$, more preferably a specific surface of 800 to 3000 $m^2/g$ and a pore volume of 0.2 to 1.0 $cm^3/g$. In the case of using the activated carbon as the support material, it is preferable to activate a surface of the activated carbon and remove an ash content from the surface of the activated carbon by immersing the activated carbon in an aqueous basic solution of ammonium hydroxide, sodium hydroxide, potassium hydroxide or the like for about 10 hours or more at around room temperature, or by pretreating the activated carbon with an acid such as nitric acid, hydrochloric acid or hydrofluoric acid, as is commonly done for use of activated carbon as a catalyst support.

It is effective to feed oxygen, chlorine, chlorinated or fluorinated hydrocarbon or the like into the reactor during the reaction for the purpose of improving the lifetime of the catalyst and the rate and yield of the reaction. In the present invention, the catalyst, when deactivated during the reaction, can be reactivated. Namely, the deactivated catalyst can be reactivated by contact treatment with an oxidizing substance such as oxygen, air or chlorine under an elevated temperature. The temperature of the contact treatment is generally 200 to 550° C., preferably 300 to 500° C. When the treatment temperature is lower than 200° C., the catalyst may remain deactivated. When the treatment temperature is higher than 550° C., the catalyst may be deteriorated and thus may not be activated properly.

There is no particular limitation on the reaction temperature in the first step. In the first step, the reaction temperature is generally in the range of 100 to 500° C., preferably 100 to 400° C., more preferably 100 to 350° C. It is not favorable that the reaction temperature exceeds 500° C. because such a high reaction temperature does to specifically bring about an improvement in the rate of the reaction and causes a decrease in the selectivity of the formation of the fluoral of the formula [2] due to generation of decomposition products.

In the first step, the molar ratio of the chloral and hydrogen fluoride supplied into the reaction zone depends on the reaction temperature. The molar ratio of the chloral to the hydrogen fluoride is generally in the range of 1:2 to 1:50, preferably 1:4 to 1:20, more preferably 1:6 to 1:15. When the amount of the hydrogen fluoride supplied is small, the yield of the target compound may decrease with decrease in the conversion rate of the reaction.

The chloral may be supplied together with a gas inert to the reaction, such as nitrogen, helium or argon, into the reaction zone in the first step. Similarly, the chloral may be supplied together with the hydrogen fluoride. It is preferable to use such an inner gas in an amount of 100 mol or less, more preferably 20 mol or less, per 1 mol of the chloral or mixture thereof as the raw material. There is no problem even when the gas inert to the reaction is not used.

In the first step, the reaction pressure is generally in the range of 0.1 to 6.0 MPa, preferably 0.1 to 3.0 MPa, more preferably 0.1 to 1.5 MPa. It is preferable to select the reaction pressure at which the organic substance such as raw material present in the reaction system do not liquefy in the reaction system.

Further, the contact time is generally in the range of 0.1 to 200 seconds, preferably 3 to 100 seconds, under standard conditions in the first step. When the contact time is short, the rate of the reaction may unfavorably decrease. When the contact time is long, there may unfavorably occur a side reaction.

The fluorination reaction proceeds with the flow of the hydrogen fluoride in the gas phase. In this reaction system, the catalyst can be held in any form such as fixed bed, fluidized bed or moving bed. The fixed-bed system is convenient and preferred.

The reaction product, obtained by the fluorination reaction in the first step and flowing out of the reactor, contains the fluoral as a predominant component. This reaction product may be used in the second step after being purified by a known method. There is no particular limitation on the method for purification of the reaction product. It is however not preferable to subject the reaction product to acid removal treatment such as washing with water in view of the fact that the fluoral is a water-soluble compound.

The hydrogen fluoride may remain contained in the fluoral-predominant product flowing out of the reactor. The hydrogen fluoride, if contained in the fluoral, can be used as a fluorination agent in the second step. Thus, the hydrogen fluoride is not necessarily positively removed from the reaction system in the first step. It is a preferable embodiment that the fluoral obtained in the first step is used in the second step as it is without specific purification operation as in the after-mentioned Examples.

[Second Step]

Next, the second step will be described below. In the second step, the 2,2,2-trifluoroacetaldehyde of the formula [2] obtained in the first step is reacted with hydrogen fluoride and trimethyl orthoformate, thereby forming 1,2,2,2-tetrafluoroethyl methyl ether of the formula [3].

The hydrogen fluoride is used in the second step. When the hydrogen fluoride remains contained in the fluoral-predominant product flowing out of the reactor in the first step, such remaining hydrogen fluoride is usable as the fluorination agent in the second step (see the after-mentioned Examples). The case in which the hydrogen fluoride remaining from the first step is utilized in the second step is the same in effect as the case in which the hydrogen fluoride is newly added in the second step. Thus, both of these cases fall within the scope of the present invention.

The amount of the hydrogen fluoride used in the second step is generally 1 equivalent or more per the fluoral obtained in the first step. In order for the reaction to proceed smoothly in the second step, the amount of the hydrogen fluoride used is preferably 2 to 10 equivalents per the fluoral. In terms of post-treatment, the amount of the hydrogen fluoride used is more preferably 3 to 6 equivalents per the fluoral. When the amount of the hydrogen fluoride used in the first step is small, some hydrogen fluoride needs to be newly added. The organic substance recovered in the first step, when containing sufficient hydrogen fluoride, can be used as it is in the second step.

In the second step, the conversion rate of the fluorination reaction is improved with the addition of the trimethyl orthoformate. For this reason, the trimethyl orthoformate is preferably added to the reaction system in the second step. The trimethyl orthoformate used can be a commercially available product (from e.g. Nippoh Chemicals Co., Ltd). With the progress of the fluorination reaction of the fluoral, not only the target compound but also water molecule are formed as indicated in the following scheme. It is assumed that the trimethyl orthoformate functions as a scavenger against the water molecule. Namely, the trimethyl orthoformate immediately undergoes hydrolysis under acidic conditions due to the presence of the hydrogen fluoride, thereby giving one methyl formate molecule and two methanol molecules. In this way, the orthoester (trimethyl orthoformate) reacts with water to form the alcohol (methanol) (that is, functions as the dehydration agent). The co-produced ester (methyl formate) can be easily separated from the target compound (1,2,2,2-tetrafluoroethyl methyl ether of the formula [3]) after the reaction.

<Fluorination>

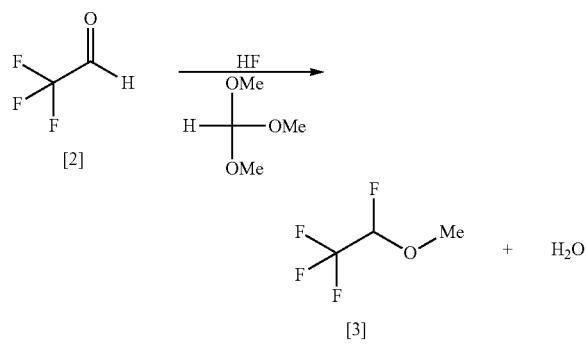

<Dehydration>

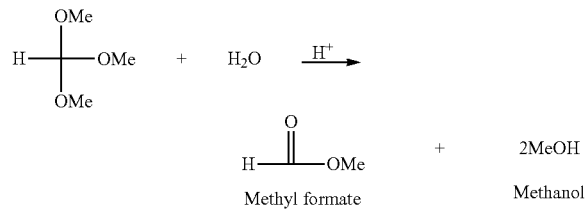

In order for the trimethyl orthoformate to function as the dehydration agent, the amount of the trimethyl orthoformate used is generally 0.2 equivalent or more, preferably 0.5 to 1.5 equivalents, per 1 equivalent of the 2,2,2-trifluoroacetaldehyde of the formula [2]. When the amount of the trimethyl orthoformate used exceeds 1.5 equivalents, the conversion of the fluoral to the target 1,2,2,2-tetrafluoroethyl methyl ether of the formula [3] may be interfered with by the formation of a compound in equilibrium with the fluoral, such as a hemiacetal of 2,2,2-trifluoroacetaldehyde hemiacetal (2,2,2-trifluoroacetaldehyde methyl hemiacetal) or a dimethylacetal of 2,2,2-trifluoroacetaldehyde hemiacetal (1,2-dimethoxy-2,2,2-trifluoroethane), under the influence of the alcohol (methanol) by-produced in the dehydration reaction. It is thus preferable to use the trimethyl orthoformate in the above-specified amount.

In the second step, the reaction is suitably conducted with the use of a solvent highly resistant to hydrogen fluoride. As the reaction solvent, an aliphatic hydrocarbon solvent, an aromatic hydrocarbon solvent, a halogenated hydrocarbon solvent, an ether solvent, an ester solvent, an amide solvent, a nitrile solvent, a sulfoxide solvent or the like is usable. Specific examples of the reaction solvent are n-hexane, cyclohexane, n-heptane, benzene, toluene, ethylbenzene, xylene, mesitylene, methylene chloride, chloroform, 1,2-dichloroethane, diethyl ether, tetrahydrofuran, diisopropyl ether, tert-butyl methyl ether, ethyl acetate, n-butyl acetate, N,N-dimethylformamide, N,N-dimethylacetamide, N-methylpyrrolidone, 1,3-dimethyl-2-imidazolidinone, acetonitrile, propionitrile and dimethyl sulfoxide. These reaction solvents can be used solely or in combination thereof.

Alternatively, the reaction may be conducted without the use of the reaction solvent. This alternative embodiment is preferable because it is advantageously possible to facilitate purification operation after the reaction and obtain the target compound with high purity only by washing operation.

In the second step, the temperature condition of the reaction is generally in the range of −50 to +100° C., preferably −20 to +50° C., more preferably 0 to +20° C.

Further, the pressure condition of the reaction is generally in the range of 0.1 to 0.9 MPa, preferably 0.1 to 0.5 MPa, more preferably 0.1 to 0.2 MPa. It is consequently preferable to conduct the reaction with the use of a pressure-proof reaction vessel made of stainless steel (SUS) etc. or a vessel made of hydrogen fluoride corrosion-resistant resin such as tetrafluoroethylene-perfluoroalkyl vinyl ether copolymer (PFA), polytetrafluoroethylene (PTFE) etc. In the case where the reaction is conducted under a temperature condition higher than or equal to the boiling point (+19.54° C.) of hydrogen fluoride, for example, the pressure-proof reaction vessel of stainless steel (SUS) etc. is preferably used.

The reaction time is generally 12 hours or less. It is preferable to determine the time at which almost all of the raw substrate material has disappeared as the end of the fluorination reaction while monitoring the progress of the fluorination reaction by any analytical means such as gas chromatography, thin-layer chromatography, liquid chromatography or nuclear magnetic resonance.

The target 1,2,2,2-tetrafluoroethyl methyl ether of the formula [3] is readily obtained by performing ordinary purification operation as post-treatment on the reaction-terminated liquid. The target compound can be purified to a higher chemical purity as required by treatment with activated carbon, distillation, recrystallization, column chromatography or the like.

[Third Step]

The third step will be next explained below. In the third step, the 1,2,2,2-tetrafluoroethyl methyl ether obtained in the second step is reacted with chlorine in the presence of a radical initiator or under light irradiation, thereby forming 1,2,2,2-tetrafluoroethyl dichloromethyl ether of the formula [4].

In the third step, the amount of the chlorine supplied is generally 1.00 to 4.00 equivalents, preferably 1.25 to 3.00 equivalents, more preferably 1.50 to 2.50 equivalents, per the 1,2,2,2-tetrafluoroethyl methyl ether of the formula [3] obtained in the second step.

The chlorination degree of the reaction substrate material varies according to the amount of the chlorine supplied. According to the inventor's finding, the generation of 1,2,2,2-tetrafluoroethyl trichloromethyl ether of the formula [6] as a by-product (highly-chlorinated compound), which is difficult to separate from the target compound (1,2,2,2-tetrafluoroethyl dichloromethyl ether of the formula [4]), is minimized by appropriately controlling the amount of the chlorine supplied.

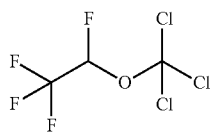

[6]

On the other hand, 1,2,2,2-tetrafluoroethyl chloromethyl ether of the formula [7] (low-chlorinated compound) is also generated as a by-product and present as a mixture with the target compound (1,2,2,2-tetrafluoroethyl dichloromethyl ether of the formula [4]). This mixture is separable by ordinary distillation operation. The low-chlorinated compound can be recovered and reused as a raw material in the chlorination reaction.

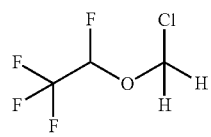

[7]

The chlorine is supplied in either gas form or liquid form into a reactor. In terms of ease of handling, it is preferable to supply the chlorine in gas form. There is no particular limitation on the method for supply of the chlorine as long as the chlorine is supplied into the reaction liquid. For example, the chlorine can be charged into the reactor at once before the initiation of the chlorination reaction, supplied in succession during the progress of the fluorination, or supplied continuously during the progress of the fluorination. In the case where the reaction is vigorous, the chlorine may be introduced as a mixture with an inert gas such as argon or nitrogen (that is, the chlorine may be "diluted" with the inert gas).

In the third step, the coexistence of the radical initiator is effective to further improve the selectivity of the chlorination of the 1,2,2,2-tetrafluoroethyl methyl ether. As the radical initiator, an organic peroxide, an azo radical initiator or the like is usable. Examples of the organic peroxide are benzoyl peroxide, ketone peroxide, peroxy ketal, hydroperoxide, dialkyl peroxide, diacyl peroxide, peroxy ester and peroxy dicarbonate. Examples of the azo radical initiator are 2,2'-azobis(2-methylpropionitrile) (abbreviated as "AIBN"), 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 2,2-azobis(2-(2-imidazolin-2-yl)propane) dihydrochloride, 2,2'-azobis(2-(2-imidazolin-2-yl)propane) disulfate and 2,2'-azobis(2-methylpropionamidine) dihydrochloride.

In the case of using the radical initiator, the amount of the radical initiator used is generally 0.01 to 20 mol %, preferably 0.1 to 10 mol %, more preferably 0.5 to 5 mol %, per 1.0 mol of the 1,2,2,2-tetrafluoroethyl methyl ether of the formula [3]. The radical initiator may be added as appropriate while monitoring the progress of the reaction. When the amount of the radical initiator used is less than 0.01 mol %, the reaction tends to be stopped in progress so that the yield of the target compound may unfavorably decrease. It is economically unfavorable to use the radical initiator in an amount exceeding 20 mol %.

In the case where the reaction is conducted under the light irradiation, on the other hand, the light irradiation is preferably performed using at least one kind of light source selected from the group consisting of a mercury lamp, an ultraviolet LED, an organic EL, an inorganic EL, an ultraviolet laser and a halogen lamp. Among other, it is preferable to use a mercury lamp as the light source.

In the third step, the reaction can be conducted with the use of a reaction solvent. (As in the after-mentioned Examples, the reaction may be conducted without the use of the reaction solvent.) As the reaction solvent, water, an aliphatic hydrocarbon solvent, an aromatic hydrocarbon solvent, an ether solvent, an ester solvent, an amide solvent, a nitrile solvent, a sulfoxide solvent or the like is usable. Specific examples of the reaction solvent are water, n-hexane, cyclohexane, n-heptane, benzene, toluene, ethylbenzene, xylene, mesitylene, methylene chloride, chloroform, 1,2-dichloroethane, diethyl ether, tetrahydrofuran, diisopropyl ether, tert-butyl methyl ether, ethyl acetate, n-butyl acetate, N,N-dimethylformamide, N,N-dimethylacetamide, N-methylpyrrolidone, 1,3-dimethyl-2-imidazolidinone, acetonitrile, propionitrile and dimethyl sulfoxide. These reaction solvents can be used solely or in combination of two or more thereof.

In the case of using water as the reaction solvent, the vaporization of the high vapor pressure compounds such as 1,2,2,2-tetrafluoroethyl methyl ether of the formula [3] and 1,2,2,2-tetrafluoroethyl chloromethyl ether of the formula [7] as the low-chlorinated compound is effectively suppressed. As a consequence, the efficiency of the reaction is expected to be improved. It is thus preferable to use the water as the reaction solvent in the third step.

The amount of the reaction solvent used in the third step is generally 10 to 1000 mass parts, preferably 10 to 500 mass parts, more preferably 25 to 250 mass parts, per 100 mass parts of the 1,2,2,2-tetrafluoroethyl methyl ether. In the case of using the water as the reaction solvent in the third step, the amount of the water used is generally 10 to 1000 mass parts, preferably 10 to 500 mass parts, more preferably 25 to 250 mass parts, per 100 mass parts of the 1,2,2,2-tetrafluoroethyl methyl ether.

In the third step, fluoride ions generated in the reaction system are efficiently captured by the addition of a fluoride ion scavenger to the reaction system. The fluoride ion scavenger is preferably at least one kind selected from the group consisting of a halide of an alkali metal, a sulfate of an alkali metal, a hydroxide of an alkaline-earth metal, a halide of an alkaline-earth metal, a sulfate of an alkaline-earth metal, a hydroxide of a Group 13 metal of the periodic table, a halide of a Group 13 metal of the periodic table and a sulfate of a Group 13 metal of the periodic table. Specific examples of the fluoride ion scavenger are sodium fluoride, sodium sulfate, calcium hydroxide, calcium chloride, calcium sulfate, aluminum hydroxide, aluminum chloride and aluminum sulfate. Among others, calcium chloride is suitably usable because it is easy to handle and high in water solubility. The calcium chloride can be in the form of at least one kind selected from the group consisting of anhydride, monohydrate, dihydrate, tetrahydrate and hexahydrate. The fluoride ion scavenger can be added as a solid. However, the effective fluoride ion capturing action of the fluoride ion scavenger is more expected when the fluoride ion scavenger is added in the form of a solution. It is thus preferable to dissolve the fluoride ion scavenger in a solvent such as water and add the resulting solution to the reaction system.

The amount of the fluoride ion scavenger used is generally 0.1 to 100 mass parts, preferably 0.5 to 50 mass parts, more preferably 1 to 25 mass parts, per 100 mass parts of the 1,2,2,2-tetafluoroethyl methyl ether.

In the third step, the reaction temperature is generally in the range of −50 to +80° C., preferably −20 to +50° C., more preferably −10 to +25° C. The lower the reaction temperature, the more improved the regioselectivity of the chlorine. It is thus preferable to conduct the reaction at room temperature or lower.

The reaction pressure is generally in the range of 0.05 to 5.0 MPa in the third step. In ordinary cases, a slightly pressurized condition of the order of 0.1 to 0.3 MPa is convenient and preferable. The reaction may alternatively be conducted under a pressure condition exceeding 5.0 MPa. However, such an excessive pressure condition causes a load on equipment. It is thus preferable to conduct in the above-specified pressure range or under atmospheric pressure. Consequently, a reaction vessel resistant to corrosion by chlorine or hydrogen chloride generated as a by-product, such as glass vessel made of silica glass, borosilicate glass etc. or resin vessel made of tetrafluoroethylene-perfluoroalkyl vinyl ether copolymer (PFA), polytetrafluoroethylene (PTFE) etc. is suitably used as the reactor.

The target compound of the third step, 1,2,2,2-tetrafluoroethyl dichloromethyl ether of the formula [4], is a precursor of desflurane useful as an inhalation anesthetic. When attempt is made to conduct fluorination of the 1,2,2,2-tetrafluoroethyl trichloromethyl ether of the formula [6] by a method disclosed in Patent Document 2 or 3, the fluorination partially proceeds to form 1,2,2,2-tetrafluoroethyl chlorodifluoromethyl ether (see the after-mentioned Reference Example 1). However, this ether compound could be an impurity difficult to separate in the process of production of desflurane. It is thus preferable that, for the production of desflurane as an inhalation anesthetic, the 1,2,2,2-tetrafluoroethyl trichloromethyl ether of the formula [6] is reduced as much as possible in the chlorination step.

In the third step, the reaction time is generally 12 hours or less. It is preferable to monitor the progress of the reaction by any analytical means such as gas chromatography, thin-layer chromatography, liquid chromatography or nuclear magnetic resonance, confirm the disappearance of the raw substrate material, and then, terminate the reaction such that the selectivity of the formation of the 1,2,2,2-tetrafluoroethyl trichloromethyl ether of the formula [6] as the difficult-to-separate highly-chlorinated compound becomes generally 10% or lower.

After the reaction, the target 1,2,2,2-tetrafluoroethyl dichloromethyl ether of the formula [4] is obtained by performing ordinary purification operation as post-treatment on the reaction-terminated liquid. The target compound can be purified to a higher chemical purity as required by treatment with activated carbon, silica gel chromatography or the like.

The 1,2,2,2-tetrafluoroethyl chloromethyl ether of the formula [7] as the low-chlorinated compound can be easily separated and recovered. The recovered 1,2,2,2-tetrafluoroethyl chloromethyl ether can be reused in the chlorination reaction and thereby converted to the target 1,2,2,2-tetraluoroforethyl dichloromethyl ether of the formula [4]. In the case of reusing the 1,2,2,2-tetrafluoroethyl chloromethyl ether of the formula [7], the chlorination reaction may be repeatedly conducted with the re-addition of the 1,2,2,2-tetrafluoroethyl methyl ether of the formula [3].

[Fourth Step]

The fourth step will be explained below. In the fourth step, the 1,2,2,2-tetrafluoroethyl dichloromethyl ether obtained in the third step is reacted with hydrogen fluoride, thereby forming 1,2,2,2-tetrafluoroethyl difluoromethyl ether (desflurane) of the formula [5].

In the fourth step, the fluorination reaction is conducted in either a liquid phase or a gas phase. The reaction conditions vary according to whether the fluorination reaction is conducted in a liquid phase or a gas phase. The liquid- and gas-phase fluorination reaction will be explained in order below.

[Liquid-Phase Fluorination Reaction]

In the fourth step, the liquid-phase fluorination reaction can be conducted with the use of a catalyst. At least one kind of catalyst selected from the group consisting of tin tetrachloride, tin dichloride, tin tetrafluoride, tin difluoride, titanium tetrachloride, antimony trichloride, antimony pentachloride and antimony pentafluoride is usable as the catalyst. These catalysts can be used solely or in combination thereof. Among others, tin tetrachloride, tin dichloride, tin tetrafluoride and tin difluoride are preferred. Particularly preferred is tin tetrachloride.

The amount of the catalyst used is generally 0.01 to 50 mass parts, preferably 0.1 to 20 mass parts, more preferably 0.5 to 10 mass parts, per 100 mass parts of the 1,2,2,2-tetrafluoroethyl dichloromethyl ether of the formula [4]. When the amount of the catalyst used exceeds 50 mass parts, the generation of tar composed of high-boiling compounds may unfavorably increase. The liquid-phase fluorination reaction may alternatively be conducted without the use of the catalyst (see the after-mentioned Examples).

The amount of the hydrogen fluoride used in the liquid-phase fluorination reaction is generally 0.1 to 100 mol, preferably 0.5 to 50 mol, more preferably 1 to 25 mol, per 1 mol of the 1,2,2,2-tetrafluoroethyl dichloromethyl ether of the formula [4]. When the amount of the hydrogen fluoride used is less than 1 mol, the conversion rate of the reaction may be low. It is economically unfavorable to use the hydrogen fluoride in an amount exceeding 100 mol.

In the fourth step, it is feasible to obtain the target desflurane by the liquid-phase fluorination reaction in which the hydrogen fluoride is reacted in the form of a "salt or complex of an organic base and the hydrogen fluoride" with the 1,2,2,2-tetrafluoroethyl dichloromethyl ether. The "salt or complex of the organic base and the hydrogen fluoride" can be prepared by mixing the organic base with the hydrogen fluoride. Alternatively, there can be used a "complex of 1 mol triethylamine and 3 mol hydrogen fluoride" or "complex of up to 30% pyridine and up to 70% hydrogen fluoride" commercially available from Sigma-Aldrich Co. LLC. (Aldrich catalog 2012-2014).

Preferred examples of the organic base in the "salt or complex of the organic base and the hydrogen fluoride" are triethylamine, diisopropylethylamine, tri-n-propylamine, tri-n-butylamine, pyridine, 2,6-lutidine, 2,4,6-collidine, 4-dimethylaminopyridine, 1,5-diazabicyclo[4.3.0]non-5-ene and 1,8-diazabicyclo[5.4.0]undec-7-ene. The organic base is not limited to these bases. An organic base commonly used for organic synthesis is applicable. Among others, triethylamine, diisopropylamine, tri-n-propylamine, tri-n-butylamine, pyridine, 2,6-lutidine, 1,5-diazabicyclo[5.4.0]non-5-ene and 1,8-diazabicyclo[5.4.0]undec-7-ene are preferred. Particularly preferred are trietylamine, diisopropylamine, tri-n-butylamine, pyridine, 2,6-lutidine and 1,8-diazabicyclo[5.4.0]undec-7-ene.

In the case of using the "salt or complex of the organic base and the hydrogen fluoride", the fluorination reaction proceeds as the hydrogen fluoride present in the salt or complex reacts with the 1,2,2,2-tetrafluoroethyl dichloromethyl ether (that is, the hydrogen fluoride in the salt or complex functions as a fluorine source to replace a chlorine atom with a fluorine atom in the same manner as the hydrogen fluorine alone). Thus, the reaction of the 1,2,2,2-tetrafluoroethyl dichloromethyl ether with the "salt or complex of the organic base and the hydrogen fluoride" is thus regarded as one example of the reaction of the 1,2,2,2-tetrafluoroethyl dichloromethyl ether with the hydrogen fluoride in the fourth step.

The molar ratio of the organic base and the hydrogen fluoride in the "salt or complex of the organic base and the hydrogen fluoride" is generally in the range of 100:1 to 1:100, preferably 50:1 to 1:50, more preferably 25:1 to 1:25.

The amount of the hydrogen fluoride contained in the "salt or complex of the organic base and the hydrogen fluoride" is generally 0.1 to 200 mol, preferably 0.5 to 100 mol, more preferably 1 to 50 mol, per 1 mol of the 1,2,2,2-tetrafluoroethyl dichloromethyl ether of the formula [4]. When the amount of the hydrogen fluoride contained is less than 0.1 mol, the conversion rate of the reaction may be low. It is economically unfavorable to use the hydrogen fluoride in an amount exceeding 200 mol.

In the fourth step, the liquid-phase fluorination reaction is conducted with the use of a solvent. As the reaction solvent, an ether solvent, an aliphatic hydrocarbon solvent, an aromatic hydrocarbon solvent, a halogenated hydrocarbon solvent, an ester solvent, an amide solvent, a nitrile solvent, a sulfoxide solvent or the like is usable.

Specific examples of the reaction solvent are diethyl ether, diisopropyl ether, dibutyl ether, tert-butyl methyl ether, tetrahydrofuran, 2-methyltetrahydrofuran, tetrahydropyrane, cyclopentyl methyl ether, n-hexane, n-heptane, n-pentane, n-nonane, n-decane, toluene, xylene, mesitylene, ethylbenzene, methylene chloride, chloroform, 1,2-dichloroethane, ethyl acetate, n-butyl acetate, N,N-dimethylformamide, N,N-dimethylacetamide, N-methylpyrrolidone, 1,3-dimethyl-2-imidazolidinone, acetonitrile, propionitrile and dimethyl sulfoxide.

Among others, tetrahydrofuran, N,N-dimethylformamide, N,N-dimethylacetamide, 1,3-dimethyl-2-imidazolidinone, acetonitrile, propionitrile and dimethyl sulfoxide are preferred. Particularly preferred are tetrahydrofuran, N,N-dimethylformamide and acetonitrile. These reaction solvents can be used solely or in combination thereof.

There is no particular limitation on the amount of the solvent used. The amount of the solvent used is generally 0.05 L (liter) or more, preferably 0.1 to 20 L, more preferably 0.1 to 10 L, per 1 mol of the 1,2,2,2-tetrafluoroethyl dichloromethyl ether of the formula [4].

The temperature condition of the liquid-phase fluorination reaction is generally in the range of −20° C. to +20° C., preferably −10 to +150° C., more preferably 0 to +100° C.

Further, the pressure condition of the liquid-phase fluorination reaction is generally in the range of 0.1 to 4.0 MPa, preferably 0.1 to 2.0 MPa, more preferably 0.1 to 1.5 MPa.

In the fourth step, the liquid-phase fluorination reaction proceeds with a high conversion rate in a temperature range of 0° C. to +50° C. and a pressure range of 0.1 to 1.0 MPa, without causing generation of a decomposition product by cleavage of an ether moiety of the substrate material or target product (desflurane), whereby the desflurane can be obtained with high selectivity. It is thus a particularly preferable embodiment to adopt the above reaction conditions.

In the case of using the "salt or complex of the organic base and the hydrogen fluoride" in the liquid-phase fluorination reaction, the fluorination reaction also proceeds with a high conversion rate in a temperature range of −10° C. to +150° C. and a pressure range of 0.1 to 2.0 MPa whereby the desflurane can be obtained with high selectivity (see the after-mentioned Example 14).

[Gas-Phase Fluorination Reaction]

In the fourth step, the gas-phase fluorination reaction can be conducted with the use of a catalyst. A metal compound-supported catalyst having, supported on a metal oxide or activated carbon, a metal compound containing at least one metal selected from the group consisting of chromium, titanium, manganese, iron, nickel, cobalt, magnesium, zirconium and antimony is usable as the catalyst. (Herein, a detailed explanation of the catalyst will be omitted herefrom because the kind and preparation method of the catalyst used in the fourth step can be the same as those of the catalyst used in the first step.)

There is no particular limitation on the reaction temperature in the gas-phase fluorination reaction. The reaction temperature is generally in the range of 100 to 500° C., preferably 100 to 400° C., more preferably 100 to 350° C. When the reaction temperature is higher than 500° C., the yield of the target compound may unfavorably decrease due to generation of a decomposition product.

In the gas-phase fluorination reaction, the molar ratio of the 1,2,2,2-tetrafluoroethyl dichloromethyl ether and hydrogen fluoride supplied into the reaction zone depends on the reaction temperature. The molar ratio of the 1,2,2,2-tetrafluoroethyl dichloromethyl ether to the hydrogen fluoride is generally in the range of 1:2 to 1:50, preferably 1:4 to 1:20, more preferably 1:5 to 1:15. When the amount of the hydrogen fluoride supplied is small, the yield of the target compound may decrease with decrease in the conversion rate of the reaction.

In the gas-phase fluorination reaction, the 1,2,2,2-tetrafluoroethyl dichloromethyl ether may be supplied together with a gas inert to the reaction, such as nitrogen, helium or argon, into the reaction zone. Similarly, the 1,2,2,2-tetrafluoroethyl dichloromethyl ether may be supplied together with the hydrogen fluoride. It is preferable to use such an inner gas in an amount of 100 mol or less, more preferably 20 mol or less, per 1 mol of the 1,2,2,2-tetrafluoroethyl dichloromethyl ether. There is no problem even when the gas inert to the reaction is not used.

The reaction pressure is generally in the range of 0.1 to 6.0 MPa, preferably 0.1 to 3.0 MPa, more preferably 0.1 to 1.5 MPa, in the gas-phase fluorination reaction. It is preferable to select the reaction pressure at which the organic substance such as raw material present in the reaction system do not liquefy in the reaction system.

In the gas-phase fluorination reaction, the contact time is generally in the range of 0.1 to 200 seconds, preferably 3 to 100 seconds, under standard conditions. When the contact time is short, the rate of the reaction may unfavorably decrease. When the contact time is long, there may unfavorably occur a side reaction.

The fluorination reaction proceeds with the flow of the hydrogen fluoride in the gas phase. In this reaction system, the catalyst can be held in any form such as fixed bed, fluidized bed or moving bed. The fixed-bed system is convenient and preferred.

In the fourth step, it is preferable to conduct the reaction with the use of a pressure-proof reaction vessel made of stainless steel (SUS) etc. or a pressure-proof reaction vessel formed with an internal lining of hydrogen fluoride corrosion-resistant resin such as tetrafluoroethylene-perfluoroalkyl vinyl ether copolymer (PFA), polytetrafluoroethylene (PTFE) etc. as the reactor.

In the fourth step, the reaction time is generally 12 hours or less, and varies according to the reaction conditions that depend on the amounts of the 1,2,2,2-tetrafluoroethyl dichloromethyl ether of the formula [4] and the hydrogen fluoride used. It is preferable to determine the time at which almost all of the raw substrate material has disappeared as the end of the reaction while monitoring the progress of the reaction by any analytical means such as gas chromatography, thin-layer chromatography, liquid chromatography or nuclear magnetic resonance.

The target desflurane is obtained with high yield by performing ordinary purification operation as post-treatment on the reaction-terminated liquid. The target compound can be purified to a higher chemical purity as required by treatment with activated carbon, distillation, recrystallization, column chromatography or the like.

The desfluorane is obtained with a higher conversion rate and higher selectivity by the fluorination reaction of the 1,2,2,-tetrafluoroethyl dichloromethyl ether in the fourth step than by the fluorination reaction of 1-chloro-2,2,2-trifluoroethyl difluoromethyl ether (isoflurane) similar to the 1,2,2,-tetrafluoroethyl dichloromethyl ether. (See Comparative Examples 1 to 4.) This result is assumed to be due to the characteristic properties of the substrate material itself. The desflurane is produced more efficiently than ever before by going through the above-mentioned first to third steps and then through the fourth step.

EXAMPLES

The present invention will be described in more detail below by way of the following examples. It should be understood that the following examples are not intended to limit the present invention thereto. Herein, the unit "%" of each composition analysis value means "area %" as determined from measurement of a raw material or product composition by gas chromatography (using FID as a detector unless otherwise specified).

Preparation Example 1: Preparation of Catalyst by Supporting Chromium Chloride on Alumina First, 3.0 L of a solution was provided by dissolving 896 g of reagent chemical $CrCl_3.6H_2O$ in pure water. In this solution, 400 g of granular alumina was immersed and left for a whole day. After that, the alumina was filtered out, kept at 100° C. in a hot air circulation-type drier and then dried for a whole day. The thus-obtained chromium-supported alumina was packed into a cylindrical reaction tube made of SUS 316L with a diameter of 4.2 cm and a length of 60 cm and equipped with an electric furnace. While flowing nitrogen gas at a flow rate of about 20 mL/min through the reaction tube, the temperature of the reaction tube was raised to 300° C. At the time when outflow of water was no longer seen, hydrogen fluoride was supplied together with the nitrogen gas into the reaction tube. The concentration of the hydrogen gas was gradually increased. When a hot spot due to fluorination of the packed chromium-supported alumina reached an outlet end of the reaction tube, the temperature of the reaction tube was raised to 350° C. This state was maintained for 5 hours, thereby preparing a catalyst.

Preparation Example 2: Preparation of Pyridine-Hydrogen Fluoride Complex

Into a 1000-mL stainless steel (SUS) autoclave reaction vessel equipped with an agitator and a pressure gauge, 158.2 g (2 mol; 1 equivalent) of pyridine was weighed and put. The reaction vessel was cooled with dry ice. After that, 200.0 g (10 mol; 5 equivalents) of hydrogen fluoride was slowly dropped into the reaction vessel at an internal vessel temperature of 20° C. or lower with caution against heat generation. After the completion of the dropping, the contents of the reaction vessel were stirred at room temperature for 1 hour. There was thus prepared a pyridine-hydrogen fluoride complex (with a molar ratio of pyridine:hydrogen fluoride=1:5).

Example 1

[Scheme 2]

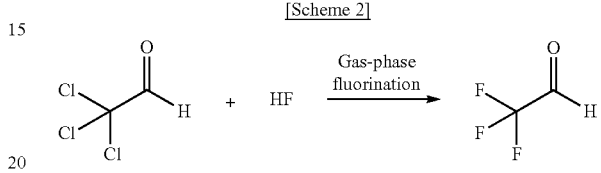

Provided was a cylindrical reaction tube with an electric furnace as a gas-phase reactor (SUS 316L-made, diameter: 2.5 cm, length: 40 cm). The reaction tube was packed with 125 mL of the catalyst prepared in Preparation Example 1. The temperature of the reaction tube was raised to 305° C. while flowing air at a flow rate of about 100 mL/min through the reaction tube. Hydrogen fluoride was introduced into the reaction tube at a rate of about 0.32 g/min for 1 hour. Subsequently, chloral as a raw material was supplied at a rate of about 0.38 g/min (contact time: 15 seconds) into the reaction tube. The reaction became stable after the lapse of 1 hour from the initiation of the reaction. In this state, a gas flowing out of the reaction tube was collected for 3 hours in a blowpipe-equipped cylinder cooled with dry ice. Then, 70.4 g of the thus-collected fluoral-containing liquid was titrated to determine the contents of hydrogen fluoride, hydrogen chloride and organic substance in the collected liquid. The content of the hydrogen fluoride was 41 mass %; the content of the hydrogen fluoride was 11 mass %; and the content of the organic substance was 90 mass %. Further, the recovery rate of the organic substance was 90% (on the basis of the mole number of the chloral supplied as the raw material). Anhydrous calcium chloride was added into a part of the recovered organic substance to remove water from the recovered organic substance. After that, the fluorination degree of the organic substance was checked by $^{19}F$-NMR. It was confirmed that the fluorination proceeded quantitatively.

Example 2

[Scheme 3]

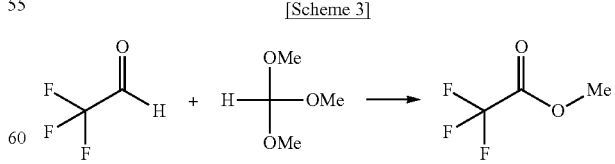

In a 250-ml reaction vessel made of tetrafluoroethylene-perfluoroalkyl vinyl ether copolymer (PFA) and equipped with a thermometer and a cooling condenser, a stirrer made of polytetrafluoroethylene (PTFE) was placed. Then, 70.4 g of the collected fluoral-containing liquid (fluoral mole number: 352 mmol) obtained in Example 1 was promptly changed into the reaction vessel. The reaction vessel was cooled, followed by adding 37.4 g (352 mmol) of methyl orthoformate to the charged liquid with caution against heat generation. The resulting liquid was reacted with stirring at room temperature for 2 hours. After that, the reaction was stopped with the addition of 60 g of water to the reaction liquid. The reaction liquid was subjected to two-layer separation. The thus-obtained organic substance was washed with 30 g of 16 mass % aqueous potassium hydroxide solution and again subjected to two-layer separation. With this, 25.7 g of the organic substance was recovered. The two-step reaction yield from Example 1 was 50%. The recovered organic substance was analyzed by GC analysis. The content of 1,2,2,2-tetrafluoroethyl methyl ether shown in the above scheme was 91.1%.

Example 3

[Scheme 4]

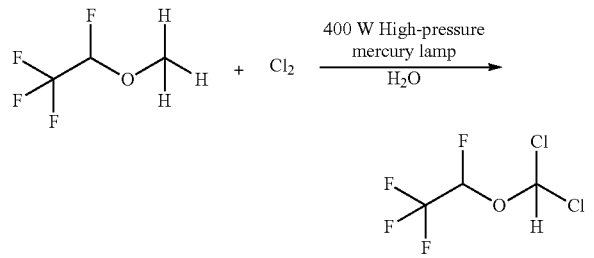

In a reaction vessel made of borosilicate glass and equipped with a thermometer and a cooling condenser, a stirrer made of polytetrafluoroethylene (PTFE) was placed. Then, 40.0 g (303 mmol; 1.00 equivalent) of 1,2,2,2-tetrafluoroethyl methyl ether and 40 g of water were weighed and put into the reaction vessel. To an outlet of the cooling condenser, attached were a water trap for absorbing hydrogen fluoride generated as a reaction by-product and a dry ice trap for recovering a volatile organic substance. Under cooling, 37.5 g (529 mmol; 1.75 equivalents) of chlorine was introduced into the reaction vessel over 4 hours with caution against heat generation while externally irradiating the reaction vessel with ultraviolet light from a 400-W high-pressure mercury lamp (manufactured by Ushio Inc.). After the introduction of the chlorine, an unreacted amount of the chlorine was purged out with nitrogen. Further, an aqueous layer was removed by two-layer separation. There was thus obtained 59.0 g of a crude reaction product. The obtained crude reaction product was analyzed by gas chromatography. It was confirmed that: 1,2,2,2-tetrafluoroethyl methyl ether shown in the above scheme was undetectable; and the crude reaction product had a composition of 38.9% 1,2,2,2-tetrafluoroethyl chloromethyl ether of the formula [7], 48.2% 1,2,2,2-tetrafluoroethyl dichloromethyl ether shown in the above scheme, 2.7% 1,2,2,2-tetrafluoroethyl trichloromethyl ether of the formula [6] and 10.2% other compounds. The organic substance trapped in the dry ice trap was in a trace amount of 0.3 g.

[Property Data]

1,2,2,2-Tetrafluoroethyl methyl ether:

$^{1}$H-NMR (400 MHz, CDCl$_3$) ☐ (ppm): 3.72 (3H, s), 5.28 (1H, dq, J=60.0, 3.2 Hz)

$^{19}$F-NMR (400 MHz, CDCl$_3$, CFCl$_3$) ☐ (ppm): −84.33 (3F, s), −146.04 (1F, d, J=60.7 Hz) 1,2,2,2-Tetrafluoroethyl dichloromethyl ether:

$^{1}$H-NMR (400 MHz, CDCl$_3$) ☐ (ppm): 6.05 (1H, dq, J=54.2, 3.2 Hz), 7.27 (1H, s)

$^{19}$F-NMR (400 MHz, CDCl$_3$, CFCl$_3$) ☐ (ppm): −83.68 (3F, s), −148.66 (1F, d, J=54.8 Hz) 1,2,2,2-Tetrafluoroethyl chloromethyl ether:

$^{1}$H-NMR (400 MHz, CDCl$_3$) ☐ (ppm): 5.57 (2H, dd, J=9.5, 9.9 Hz), 5.73 (1H, dq, J=59.4, 3.2 Hz)

$^{19}$F-NMR (400 MHz, CDCl$_3$, CFCl$_3$) ☐ (ppm): −83.91 (3F, s), −152.60 (1F, d, J=57.7 Hz)

1,2,2,2-Tetrafluoroethyl trichloromethyl ether:

$^{1}$H-NMR (400 MHz, CDCl$_3$) ☐ (ppm): 6.10 (1H, dq, J=52.7, 3.2 Hz)

$^{19}$F-NMR (400 MHz, CDCl$_3$, CFCl$_3$) ☐ (ppm): −83.38 (3F, s), −148.06 (1F, d, J=52.2 Hz)

Example 4

[Scheme 5]

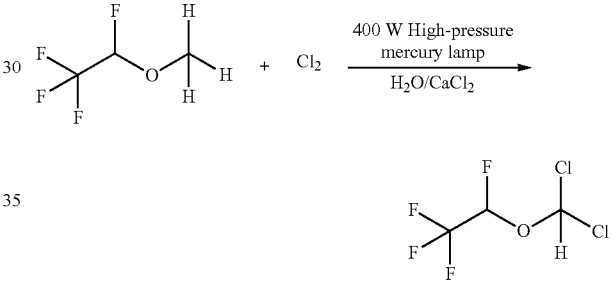

In a reaction vessel made of borosilicate glass and equipped with a thermometer and a cooling condenser, a stirrer made of polytetrafluoroethylene (PTFE) was placed. Then, 30 g (227 mmol; 1.00 equivalent) of 1,2,2,2-tetrafluoroethyl methyl ether, 15 g of water and 1.5 g of anhydrous calcium chloride were weighed and put into the reaction vessel. Under cooling, 33 g (465 mmol; 2.00 equivalents) of chlorine was introduced into the reaction vessel over 4 hours with caution against heat generation while externally irradiating the reaction vessel with ultraviolet light from a 400-W high-pressure mercury lamp (manufactured by Ushio Inc.). After the introduction of the chorine, an unreacted amount of the chlorine was purged out with nitrogen. There was thus obtained 39 g of a crude reaction product. The obtained crude reaction product was analyzed by gas chromatography. It was confirmed that: 1,2,2,2-tetrafluoroethyl methyl ether shown in the above scheme was undetectable; and the crude reaction product had a composition of 26.9% 1,2,2,2-tetrafluoroethyl chloromethyl ether of the formula [7], 58.3% 1,2,2,2-tetrafluoroethyl dichloromethyl ether shown in the above scheme, 6.4% 1,2,2,2-tetrafluoroethyl trichloromethyl ether of the formula [6] and 8.4% other compounds. Further, the concentration of fluoride ions in the crude reaction product was determined to be 3 ppm by the ion electrode method.

Example 5

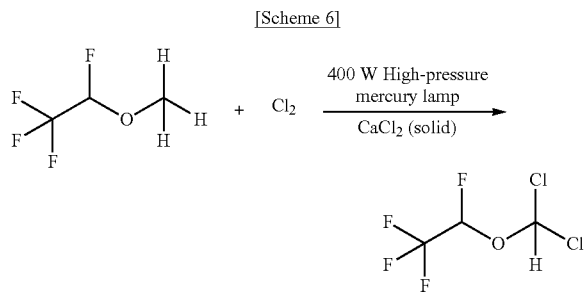

[Scheme 6]

In a reaction vessel of made of borosilicate glass and equipped with a thermometer and a cooling condenser, a stirrer made of polytetrafluoroethylene (PTFE) was placed. Then, 30 g (227 mmol; 1.00 equivalent) of 1,2,2,2-tetrafluoroethyl methyl ether and 1.5 g of anhydrous calcium chloride were weighed and put into the reaction vessel. Under cooling, 33 g (465 mmol; 2.00 equivalents) of chlorine was introduced into the reaction vessel over 4 hours with caution against heat generation while externally irradiating the reaction vessel with ultraviolet light from a 400-W high-pressure mercury lamp (manufactured by Ushio Inc.). After the introduction of the chlorine, an unreacted amount of the chlorine was purged out with nitrogen. There was thus obtained 39 g of a crude reaction product. The obtained crude reaction product was analyzed by gas chromatography. It was confirmed that: 1,2,2,2-tetrafloroethyl methyl ether shown in the above scheme was undetectable; and the crude reaction product had a composition of 18.7% 1,2,2,2-tetrafluoroethyl chloromethyl ether of the formula [7], 61.2% 1,2,2,2-tetrafluoroethyl dichloromethyl ether shown in the above scheme, 8.9% 1,2,2,2-tetrafluoroethyl trichloromethyl ether of the formula [6] and 11.2% other compounds. Further, the concentration of fluoride ions in the crude reaction product was determined to be 5 ppm by the ion electrode method.

Example 6

[Scheme 7]

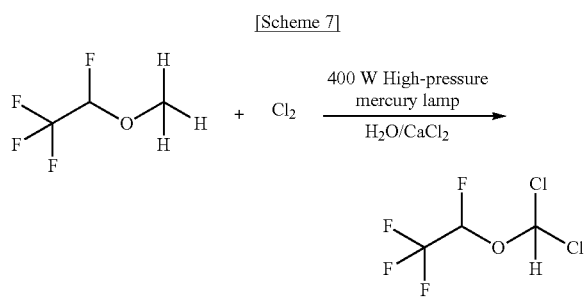

In a reaction vessel made of borosilicate glass and equipped with a thermometer and a cooling condenser, a stirrer made of polytetrafluoroethylene (PTFE) was placed. Then, 400 g (3.03 mol; 1.00 equivalent) of 1,2,2,2-tetrafluoroethyl methyl ether, 285 g of water and 15 g of anhydrous calcium chloride were weighed and put into the reaction vessel. Under cooling, 379 g (5.35 mol; 1.76 equivalents) of chlorine was introduced into the reaction vessel over 5 hours with caution against heat generation while externally irradiating the reaction vessel with ultraviolet light from a 400-W high-pressure mercury lamp (manufactured by Ushio Inc.). After the introduction of the chlorine, an unreacted amount of the chlorine was purged out with nitrogen. There was thus obtained 510 g of a crude reaction product. The obtained crude reaction product was analyzed by gas chromatography. It was confirmed that: 1,2,2,2-tetrafluoroethyl methyl ether shown in the above scheme was undetectable; and the crude reaction product had a composition of 33.5% 1,2,2,2-tetrafluoroethyl chloromethyl ether of the formula [7], 52.6% 1,2,2,2-tetrafluoroethyl dichloromethyl ether shown in the above scheme, 4.4% 1,2,2,2-tetrafluoroethyl trichloromethyl ether and 9.5% other compounds. Further, the concentration of fluoride ions in the crude reaction product was determined to be 5 ppm by the ion electrode method. The crude reaction product was subjected to fractionation by a distillation column with a theoretical plate number of 10, thereby yielding 148 g of an initial fraction containing 97.2% of the 1,2,2,2-tetrafluoroethyl chloromethyl ether of the formula [7] and 226 g of a main fraction containing 96.8% of the 1,2,2,2-tetrafluoroethyl dichloromethyl ether shown in the above scheme. The content of the 1,2,2,2-tetrafluoroethyl trichloromethyl ether of the formula [6] in the main fraction was 1.0% or less. The recovery rate of the low-chlorinated compound in the initial fraction was 29%. The recovery rate of the target compound in the main fraction was 37%.

Example 7

[Scheme 8]

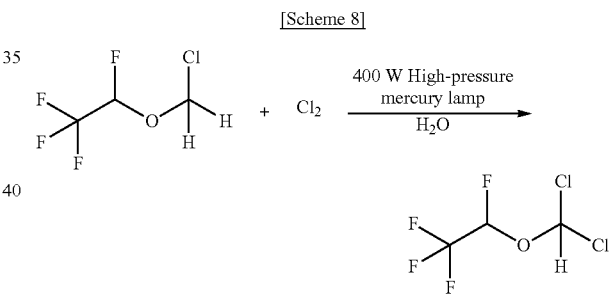

In a reaction vessel made of borosilicate glass and equipped with a thermometer and a cooling condenser, a stirrer made of polytetrafluoroethylene (PTFE) was placed. Then, 20 g (120 mmol; 1.00 equivalent) of the 1,2,2,2-tetrafluoroethyl chloromethyl ether of the formula [7] recovered in Example 6 and 10 g of water were weighed and put into the reaction vessel. Under cooling, 8 g (113 mmol; 0.95 equivalent) of chlorine was introduced into the reaction vessel over 1 hour with caution against heat generation while externally irradiating the reaction vessel with ultraviolet light from a 400-W high-pressure mercury lamp (manufactured by Ushio Inc.). After the introduction of the chlorine, an unreacted amount of the chlorine was purged out with nitrogen. There was thus obtained 22 g of a crude reaction product. The obtained crude reaction product was analyzed by gas chromatography. It was confirmed that the crude reaction product had a composition of 27.9% 1,2,2,2-tetrafluoroethyl chloromethyl ether of the formula [7], 64.7% 1,2,2,2-tetrafluoroethyl dichloromethyl ether shown in the above scheme, 5.3% 1,2,2,2-tetrafloroethyl trichloromethyl ether of the formula [6] and 2.1% other compounds.

Example 8

[Scheme 9]

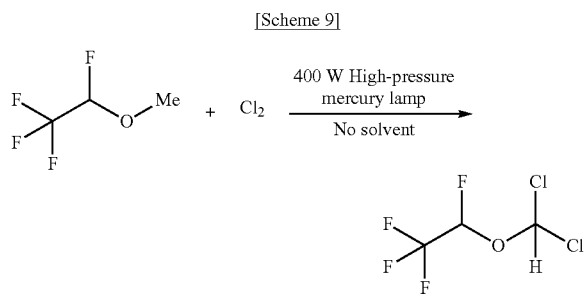

In a reaction vessel made of borosilicate glass and equipped with a thermometer and a cooling condenser, a stirrer made of polytetrafluoroethylene (PTFE) was placed. Then, 150 g (1.14 mol; 1.00 equivalent) of 1,2,2,2-tetrafluoroethyl methyl ether shown in the above scheme was weighed and put into the reaction vessel. Under cooling, 178 g (2.51 mol; 2.20 equivalents) of chlorine was introduced into the reaction vessel over 5 hours with caution against heat generation while externally irradiating the reaction vessel with ultraviolet light from a 400-W high-pressure mercury lamp (manufactured by Ushio Inc.). After the introduction of the chlorine, an unreacted amount of the chlorine was purged out with nitrogen. There was thus obtained 199 g of a crude reaction product. The crude reaction product was subjected to fractionation by a distillation column with a theoretical plate number of 10, thereby yielding 114 g of a fraction containing 1,2,2,2-tetrafluoroethyl dichloromethyl ether shown in the above formula with a GC purity of 92.9%. The recovery rate of this ether compound from the reaction was 50%.

Example 9

[Scheme 10]

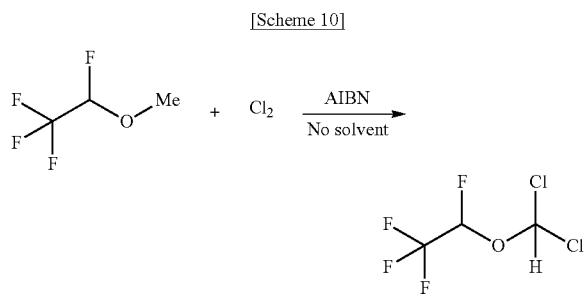

In a reaction vessel made of borosilicate glass and equipped with a thermometer and a cooling condenser, a stirrer made of polytetrafluoroethylene (PTFE) was placed. Then, 50 g (379 mmol; 1.00 equivalent) of 1,2,2,2-tetrafluoroethyl methyl ether shown in the above scheme and 1.2 g (7.6 mmol; 2 mol %) of AIBN were weighed and put into the reaction vessel. After the reaction vessel was heated to a temperature of 40° C. in an oil bath, 107 g (1.52 mol; 4.00 equivalents) of chlorine was introduced into the reaction vessel with caution against heat generation. During the reaction, the temperature of the oil bath was raised according to the chlorination degree of the substrate material so that the internal temperature of the reaction vessel finally reached 66° C. After the introduction of the chlorine, an unreacted amount of the chlorine was purged out with nitrogen. The thus-obtained reaction liquid was analyzed by GC analysis. It was confirmed that the reaction liquid had a composition of 59.7 GC % 1,2,2,2-tetrafluoroethyl dichloromethyl ether shown in the above scheme, 15.0 GC % low-chlorinated compound (1,2,2,2-tetrafluoroethyl chloromethyl ether), 16.9 GC % highly-chlorinated compound (1,2,2,2-tetrafluoroethyl trichloromethyl ether) and 8.4% other compounds.

Example 10

[Scheme 11]

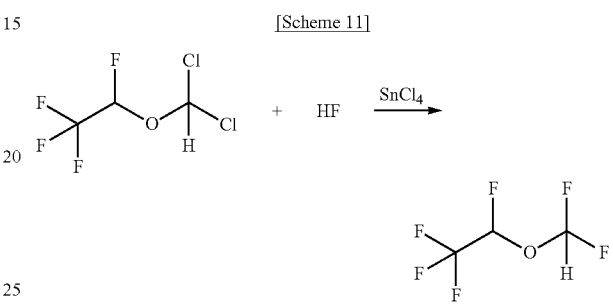

In a 100-mL autoclave reaction vessel (SUS 316L) equipped with a pressure gauge and a cooling condenser, a stirrer made of polytetrafluoroethylene (PTFE) was placed. Then, 10 g (49.8 mmol; 1.00 equivalent) of 1,2,2,2-tetrafluoroethyl dichloromethyl ether shown in the above scheme and 1.3 g (4.99 mmol; 10 mol %) of tin tetrachloride were weighed and put into the reaction vessel. After the reaction vessel was cooled in an ice bath, 20.0 g (1.00 mol; 20.0 equivalents) of hydrogen fluoride was charged at once into the reaction vessel. The temperature of the reaction vessel was raised to 80° C. The resulting liquid was stirred with heating for 8 hours while discharging by-produced hydrogen chloride out of the reaction system through the condenser to maintain the reaction pressure at 1.0 MPa. After that, the reaction was stopped by pouring all the reaction liquid in ice water. The reaction liquid was subjected to two-layer separation, thereby recovering 7.8 g of an organic substance. The recovery rate of the organic substance was 93%. The purity of the obtained target desflurane (see the above formula) was 98.0%.

Example 11

[Scheme 12]

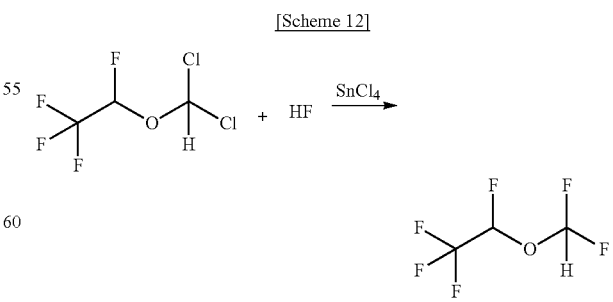

Into a 500-mL autoclave reaction vessel (SUS 316L-made) equipped with an agitator, a pressure gauge and a cooling condenser, 201 g (1.00 mol; 1.00 equivalent) of 1,2,2,2-tetrafluoroethyl dichloromethyl ether shown in the above scheme and 2.61 g (10.0 mmol; 1.0 mol %) of tin tetrachloride were weighed and put. After the reaction vessel was cooled in an ice bath, 49.8 g (2.49 mol; 2.5 equivalents) of hydrogen fluoride was charged at once into the reaction vessel. The temperature of the reaction vessel was gradually raised to 20° C. with caution against heat generation. Subsequently, the resulting liquid was reacted for 12 hours while discharging by-produced hydrogen chloride out of the reaction system through the cooling condenser to maintain the reaction pressure at around 0.1 MPa (atmospheric pressure). After that, the reaction was stopped by pouring all the reaction liquid in ice water. The reaction liquid was subjected to two-layer separation, thereby recovering 163 g of an organic substance. The recovery rate of the organic substance was 97.0%. The purity of the obtained target desflurane (see the above formula) was 93.3%.

Example 12

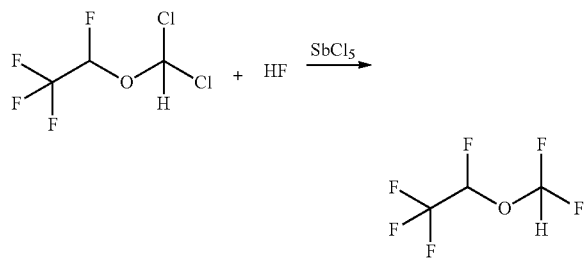

In a 100-mL autoclave reaction vessel (SUS 316L-made) equipped with a pressure gauge and a cooling condenser, a stirrer made of polytetrafluoroethylene (PTFE) was placed. Then, 20 g (99.5 mmol; 1.00 equivalent) of 1,2,2,2-tetrafluoroethyl dichloromethyl ether shown in the above scheme and 0.36 g (1.20 mmol; 1.2 mol %) of antimony pentachloride were weighed and put. After the reaction vessel was cooled in an ice bath, 8.8 g (440 mmol; 4.4 equivalents) of hydrogen fluoride was charged at once into the reaction vessel. The temperature of the reaction vessel was gradually raised to 15° C. with caution against heat generation. Subsequently, the resulting liquid was reacted for 6 hours while discharging by-produced hydrogen chloride out of the reaction system through the cooling condenser to maintain the reaction pressure at around 0.1 MPa (atmospheric pressure). After that, the reaction was stopped by pouring all the reaction liquid in ice water. The reaction liquid was subjected to two-layer separation, thereby recovering 12.1 g of an organic substance. The recovery rate of the organic substance was 72.4%. The purity of the obtained target desflurane (see the above formula) was 96.9%.

Example 13

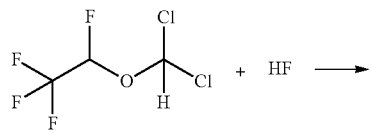

-continued

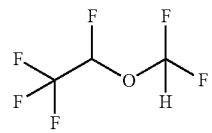

In a 100-mL autoclave reaction vessel (SUS 316L-made) equipped with a pressure gauge and a cooling condenser, a stirrer made of polytetrafluoroethylene (PTFE) was placed. Then, 10 g (49.8 mmol; 1.00 equivalent) of 1,2,2,2-tetrafluoroethyl dichloromethyl ether shown in the above scheme was weighed and put into the reaction vessel. After the reaction vessel was cooled in an ice bath, 20.0 g (1.00 mol; 20.0 equivalent) of hydrogen fluoride was charged at once into the reaction vessel. The temperature of the reaction vessel was raised to 80° C. The resulting liquid was stirred with heating for 8 hours while discharging by-produced hydrogen chloride out of the reaction system through the cooling condenser to maintain the reaction pressure at 1.0 MPa. After that, the reaction was stopped by pouring all the reaction liquid in ice water. The reaction liquid was subjected to two-layer separation, thereby recovering 7.7 g of an organic substance. The recovery rate of the organic substance was 92%. The purity of the obtained target desflurane (see the above formula) was 71.3%. Further, it was found that the recovered organic substance contained 26.1% of 1,2,2,2-tetrafluoroethyl fluorochloromethyl ether of the formula [8] (as a reaction intermediate formed by monofluorination of the 1,2,2,2-tetrafluoroethyl dichloromethyl ether).

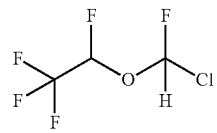

[8]

Example 14

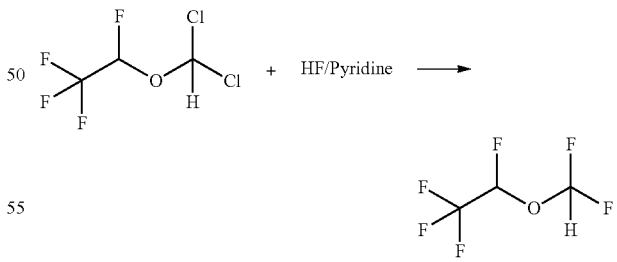

Into a 500-mL autoclave reaction vessel made of stainless steel (SUS) and equipped with an agitator, a pressure gauge and a condenser, 39.9 g (199 mmol; 1 equivalent) of 1,2,2,2-tetrafluoroethyl dichloromethyl ether shown in the above scheme was weighed and put. The reaction vessel was cooled with dry ice. Under cooling, 71.0 g (396 mmol; 1.99 equivalents) of the pyridine-hydrogen fluoride complex (molar ratio of pyridine:hydrogen fluoride=1:5) prepared in Preparation Example 1 was introduced into the reaction vessel with caution against heat generation. The reaction was then initiated by raising the temperature of the reaction vessel to 120° C. After the temperature rise, the reaction was conducted for 15 hours while discharging by-produced hydrogen chloride out of the reaction system through the condenser to maintain the reaction pressure at 1.8 MPa. The reaction was stopped by pouring all the reaction liquid in ice water. The reaction liquid was subjected to two-layer separation, thereby recovering 27.1 g of an organic substance. The recovery rate of the organic substance was 81.1%. The purity of the obtained target desflurane (see the above scheme) was 90.2%.

Further, the temperature of the reaction tube was changed as shown in TABLE 1 (Examples 16 and 17). After the reaction became stable, the gas flowing out of the reaction tube was blown into water to remove an acidic gas component. The thus-obtained product gas was analyzed by gas chromatography.

The results of Examples 15-17 are shown in TABLE 1.

TABLE 1

|  | Reaction temp. ° C. | Contact time sec. | GC% Raw material [4] | Desflurane | Reaction intermediate [8] | Conversion rate % | Selectivity % |
|---|---|---|---|---|---|---|---|
| Example 15 | 180 | 25 | 0.2 | 88.8 | 2.5 | 99.8 | 96.8 |
| Example 16 | 150 | 26 | 2.3 | 62.2 | 26.5 | 97.4 | 69.4 |
| Example 17 | 120 | 22 | 38.0 | 18.6 | 33.7 | 58.7 | 34.5 |

Raw material [4]: 1,2,2,2-Tetrafluoroethyl dichloromethyl ether
Reaction intermediate [8]: 1,2,2,2,-Tetrafluoroethyl fluorochloromethyl ether $$\text{Conversion rate: } \frac{(GC\% \text{ of raw material used}) - (GC\% \text{ of raw material remaining after reaction})}{GC \text{ purity of raw material used}} \times 100$$

$$\text{Selectivity: } \frac{GC\% \text{ of target compound obtained by reaction}}{(GC\% \text{ of raw material used}) - (GC\% \text{ of raw material remaining after reaction})} \times 100$$

Examples 15-17

[Scheme 16]

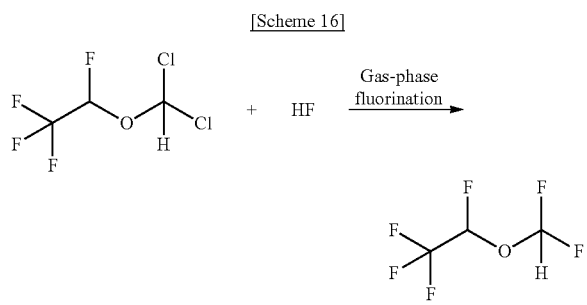

Provided was a cylindrical reaction tube with an electric furnace as a gas-phase reactor (SUS 316L-made, diameter: 2.5 cm, length: 40 cm). The reaction tube was packed with 100 mL of the catalyst prepared in Preparation Example 1. The temperature of the reaction tube was raised to 180° C. while flowing nitrogen gas at a flow rate of about 10 mL/min through the reaction tube. Hydrogen fluoride was introduced into the reaction tube at a rate of about 0.1 g/min for 1 hour. Subsequently, 1,2,2,2-tetrafluoroethyl dichloromethyl ether (91.9 GC %) as a raw material was supplied at a rate of about 0.1 g/min (contact time: 25 seconds) into the reaction tube. The reaction became stable after the lapse of 1 hour from the initiation of the reaction. In this state, a gas flowing out of the reaction tube was blown into water to remove an acidic gas component. The thus-obtained product gas was analyzed by gas chromatography.

Example 18

Provided was the same gas-phase reactor as in Examples 15 to 17. The temperature of the reaction tube was set to 180° C. Hydrogen fluoride was introduced into the reaction tube at a rate of about 0.1 g/min for 1 hour. Subsequently, 1,2,2,2-tetrafluoroethyl dichloromethyl ether (94.6 GC %) as a raw material was supplied into the reaction tube at a rate of 0.1 to 0.2 g/min (contact time: 20 to 25 seconds) for 4.5 hours. Then, a gas flowing out of the reaction tube was blown into water to remove an acidic gas component. An organic substance flowing out of the water trap was collected in a dry ice trap. With this, 23.3 g of the organic substance was recovered. The organic substance was analyzed by GC analysis. It was confirmed that desflurane was obtained with a purity of 96.8%. The yield of the organic substance was 91% (on the basis of the mole number of the 1,2,2,2-tetrafluoroethyl dichloromethyl ether supplied as the raw material).

Reference Example 1

[Scheme 17]

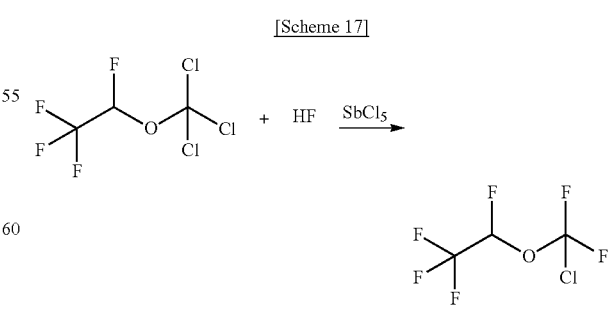

In a 100-mL autoclave reaction vessel made of stainless steel (SUS) and equipped with a pressure gauge, a stirrer made of polytetrafluoroethylene (PTFE) was placed. Under dry ice cooling, 5.0 g (21.2 mmol) of 1,2,2,2-tetrafluoroethyl trichloromethyl ether shown in the above scheme, 8.5 g (425 mmol) of hydrogen fluoride and 329 mg (1.1 mmol) of antimony pentachloride were weighed and put into the reaction vessel. The temperature of the reaction vessel was naturally raised. Subsequently, the resulting liquid was reacted with stirring for 8 hours under a temperature condition from room temperature to 80° C. After the reaction, the reaction pressure of 0.90 MPa was released. The reaction liquid was washed with water and subjected to two-layer separation. The thus-obtained organic substance was analyzed by gas chromatography. It was confirmed that 1,2,2,2-tetrafluoroethyl difluorochloromethyl ether shown in the above scheme was obtained with a purity of 90GC %.

[Property Data]

1,2,2,2-Tegrafluoroethyl difluorochloromethyl ether:

$^1$H-NMR (400 MHz, CDCl$_3$) □ (ppm): 5.96 (1H, dq, J=53.4, 2.8 Hz)

$^{19}$F-NMR (400 MHz, CDCl$_3$, CFCl$_3$) □ (ppm): −28.93 (1F, d, J=86.8 Hz), −29.95 (1F, d, J=92.8 Hz), −83.41 (3F, s), −146.75 (1F, d, J=54.8 Hz)

Comparative Examples 1-4

[Scheme 18]

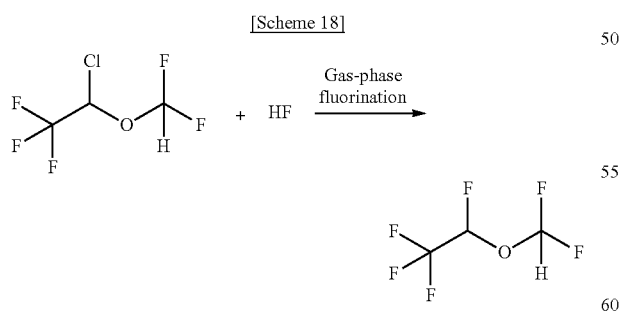

Provided was a cylindrical reaction tube with an electric furnace as a gas-phase reactor (SUS 316L-made, diameter: 2.5 cm, length: 40 cm). The reaction tube was packed with 100 mL of the catalyst prepared in Preparation Example 1. The temperature of the reaction tube was raised to 180° C. while flowing nitrogen gas at a flow rate of about 10 mL/min through the reaction tube. Hydrogen fluoride was introduced into the reaction tube at a rate of about 0.1 g/min for 1 hour. Subsequently, 1-chloro-2,2,2-trifluoroethyl difluoromethyl ether (isoflurane; 99.9 GC %) as a raw material was supplied at a rate of about 0.1 g/min (contact time: 25 seconds) into the reaction tube. The reaction became stable after the lapse of 1 hour from the initiation of the reaction. In this state, a gas flowing out of the reaction tube was blown into water to remove an acidic gas component. The thus-obtained product gas was analyzed by gas chromatography.

Further, the temperature of the reaction tube was changed as shown in TABLE 2 (Comparative Examples 2, 3 and 4). After the reaction became stable, the gas flowing out of the reaction tube was blown into water to remove an acidic gas component. The thus-obtained product gas was analyzed by gas chromatography.

The results of Comparative Examples 1-4 are shown in TABLE 2.

TABLE 2

| | Reaction temp. °C. | Contact time sec. | GC% | | | Conversion rate % | Selectivity % |
|---|---|---|---|---|---|---|---|
| | | | Isoflurane | Desflurane | Decomposition product [9] | | |
| Comparative Example 1 | 180 | 20 | 96.8 | 2.7 | <0.1 | 3.2 | 84.3 |
| Comparative Example 2 | 220 | 15 | 94.5 | 4.9 | <0.1 | 5.4 | 90.7 |
| Comparative Example 3 | 300 | 18 | 34.5 | 57.9 | 6.0 | 65.6 | 88.4 |
| Comparative Example 4 | 320 | 19 | 8.0 | 72.7 | 14.4 | 92.0 | 79.1 |

Decomposition product [9]: 1,1,1,2-Tetrafluoro-2-chloroethane

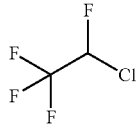

[9]

INDUSTRIAL APPLICABILITY

The target compound of the present invention, 1,2,2,2-tetrafluoroethyl difluoromethyl ether (desflurane), is useful as an inhalation anesthetic.

The invention claimed is:

1. A production method of 1,2,2,2-tetrafloroethyl difluoromethyl ether, comprising the following four steps:

a first step of reacting 2,2,2-trichloroacetaldehyde of the formula [1] with hydrogen fluoride in a gas phase in the presence of a catalyst, thereby obtaining 2,2,2-trifluoroacetaldehyde of the formula [2]

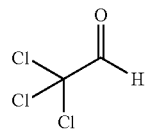

[1]

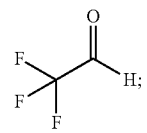

[2]

a second step of reacting the 2,2,2-trifluoroacetaldehyde obtained in the first step with hydrogen fluoride and trimethyl orthoformate, thereby obtaining 1,2,2,2-tetrafluoroethyl methyl ether of the formula [3]

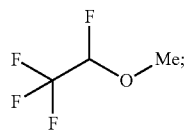

[3]

a third step of reacting the 1,2,2,2-tetrafluoroethyl methyl ether obtained in the second step with chlorine (Cl$_2$) in the presence of a radical initiator or under light irradiation, thereby obtaining 1,2,2,2-tetrafluoroethyl dichloromethyl ether of the formula [4]

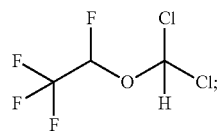

[4]

and a fourth step of reacting the 1,2,2,2-tetrafluoroethyl dichloromethyl ether obtained in the third step with hydrogen fluoride, thereby obtaining 1,2,2,2-tetrafloroethyl difluoromethyl ether of the formula [5]

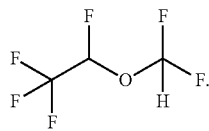

[5]

2. The production method according to claim 1, wherein the catalyst used in the first step is a metal compound-supported catalyst having, supported on a metal oxide or activated carbon, a metal compound containing at least one metal selected from the group consisting of chromium, titanium, manganese, iron, nickel, cobalt, magnesium, zirconium and antimony.

3. The production method according to claim 2, wherein the metal compound is at least one kind of metal halide or metal oxyhalide selected from the group consisting of a fluoride, a chloride, a fluorochloride, an oxyfluoride, an oxychloride and an oxyfluorochloride of the at least one metal.

4. The production method according to claim 2, wherein the metal oxide is at least one kind selected from the group consisting of alumina, zirconia, titania, chromia and magnesia.

5. The production method according to claim 1, wherein the 2,2,2-trifluoroacetaldehyde obtained in the first step is used as it is, without purification operation, as a raw material in the second step.

6. The production method according to claim 1, wherein, in the second step, the reacting is conducted without the use of an organic solvent.

7. The production method according to claim 1, wherein the radical initiator used in the third step is at least one kind selected from the group consisting of an organic peroxide and an azo-based radical initiator.

8. The production method according to claim 1, wherein the light irradiation used in the third step is at least one kind selected from the group consisting of those from a mercury lamp, an ultraviolet LED, an organic EL, an inorganic EL, an ultraviolet laser and a halogen lamp.

9. The production method according to claim 1, wherein, in the third step, the reacting is conducted in the presence of a fluoride ion scavenger.

10. The production method according to claim 9, wherein fluoride ion scavenger is at least one kind selected from the group consisting of a halide of an alkali metal, a sulfate of an alkali metal, a hydroxide of an alkaline-earth metal, a halide of an alkaline-earth metal, a sulfate of an alkaline-earth metal, a hydroxide of a Group 13 metal of the periodic table, a halide of a Group 13 metal of the periodic table and a sulfate of a Group 13 metal of the periodic table.

11. The production method according to claim 1, wherein, in the third step, the reacting is conducted with the use of a reaction solvent.

12. The production method according to claim 1, wherein, in the third step, the 1,2,2,2-tetrafluoroethyl dichloromethyl ether of the formula [4] is obtained as a mixture thereof with a 1,2,2,2-tetrafluoroethyl chloromethyl ether of the formula [7]

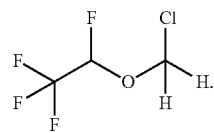

[7]

13. The production method according to claim 12, further comprising performing distillation purification on the mixture to separate and remove the 1,2,2,2-tetrafluoroethyl chloromethyl ether of the formula [7] from the mixture.

14. The production method according to claim 13, wherein the 1,2,2,2-tetrafluoroethyl chloromethyl ether of the formula [7] separated and removed by the distillation purification is recovered and used as a raw material in the third step.

15. The production method according to claim 1, wherein, in the fourth step, the reacting is conducted in a gas phase.

16. The production method according to claim 1, wherein, in the fourth step, the reacting is conducted in the presence of a catalyst.

17. The production method according to claim 16, wherein the catalyst used in the fourth step is at least one kind selected from the group consisting of tin tetrachloride, tin dichloride, tin tetrafluoride, tin difluoride, titanium tetrachloride, antimony trichloride, antimony pentachloride and antimony pentafluoride.

18. The production method according to claim 1, wherein, in the fourth step, the reacting is conducted without the presence of a catalyst.

19. The production method according to claim 1, wherein, in the fourth step, the reacting is conducted in a liquid phase.

20. The production method according to claim 19, wherein in the fourth step, the reacting is conducted in the liquid phase in a temperature range of −10° C. to +150° C. and a pressure range of 0.1 MPa to 2.0 MPa.

21. The production method according to claim 1, wherein, in the fourth step, the reacting is conducted by reacting the 1,2,2,2-tetrafluoroethyl dichloromethyl ether with a "salt or complex of an organic base and the hydrogen fluoride" in the liquid phase.

22. The production method according to claim 21, wherein the organic base in the "salt or complex of the organic base and the hydrogen fluoride" is at least one kind selected from the group consisting of triethylamine, diisopropylethylamine, tri-n-butylamine, pyridine, 2,6-lutidine and 1,8-diazabicyclo[5.4.0]undec-7-ene.

* * * * *